United States Patent [19]

Shaw

[11] Patent Number: 5,686,311
[45] Date of Patent: Nov. 11, 1997

[54] DIAGNOSIS OF AUTISM AND TREATMENT THEREFOR

[75] Inventor: William Shaw, Shawnee, Kans.

[73] Assignee: The Children's Mercy Hospital, Kansas City, Mo.

[21] Appl. No.: 494,200

[22] Filed: Jun. 23, 1995

[51] Int. Cl.$^6$ ................................. G01N 33/48
[52] U.S. Cl. .................. 436/86; 436/91; 436/98; 436/811
[58] Field of Search .............. 436/86, 91, 98, 436/811

[56] References Cited

PUBLICATIONS

Shaw et al. "Increased Urinary Excretion . . . with Autistic Features", Clin. Chem. 41/8, 1094–1104(1995).
BIOSIS 87:384546.

*Primary Examiner*—Lyle A. Alexander
*Attorney, Agent, or Firm*—Hovey,Williams, Timmons & Collins

[57] ABSTRACT

A method for diagnosing the likelihood of autism in patients is provided which comprises first obtaining from the patient a sample of body fluid such as urine and analyzing the sample to determine the quantity therein of at least one marker compound selected from the group consisting of citramalic acid, 5-hydroxy-methyl-2-furoic acid, 3-oxo-glutaric acid, furan-2,5-dicarboxylic acid, tartaric acid, furancarbonylglycine, arabinose, dihydroxyphenylpropionic acid, carboxycitric acid and phenylcarboxylic acid; if the quantities of one or more of the compounds are abnormally high, as compared with the urine of non-autistic individuals, an ultimate diagnosis of autism is likely. The invention also pertains to a method of treating autistic patients by administration of antifungal drugs, in order to ameliorate the clinical symptoms of autism.

7 Claims, 28 Drawing Sheets

Fig. 27. N = 20 (NORMAL) N = 97 (AUTISTIC)

DIAGNOSIS OF AUTISM AND TREATMENT THEREFOR

BACKGROUND OF THE INVENTION

1. Field of the Invention

The present invention is broadly concerned with an improved method to aid in the diagnosis of autism, and a corresponding method of treating this condition in order to ameliorate the symptoms thereof. More particularly, the invention pertains to a diagnosis method wherein a body fluid sample (e.g., urine) is obtained and quantified for the presence of certain marker compounds such as tartaric acid; abnormally high quantities of one or more of the marker compounds is an indication of autism. In a treatment protocol, a patient suffering from autism is given an antifungal drug, which reduces the quantities of marker compounds and ameliorates the symptoms of autism.

2. Description of the Prior Art

Childhood autism is the most characteristic group of the broader persuasive developmental disorder category of childhood diseases. The cause of autism is unknown except for a small subgroup due to adenylosuccinic aciduria, a defect in purine metabolism. Autism is characterized by a behavioral syndrome often recognized between two and three years of age. The core of the syndrome is a deviant and/or retarded development of cognitive capacities and skills necessary for social relations, communication, fantasy, and symbolic thinking. Almost all autistic children do not reach independence as adults and 75% are deemed mentally retarded. Taurine aspartate, and glutonate are reported to be significantly elevated in the plasma of a significant fraction of autistic persons, and some have metabolic acidosis. Diagnosis of autism presents difficulties in its own right, and a number of modalities have been proposed primarily based upon psychiatric evaluations.

A number of different therapies have been attempted in an effort to cure autism or at least lessen the clinical symptoms thereof. Such have included drug therapies as well as psychiatric care and attempted counseling. In general, results of such treatments have been disappointing, and autism remains very difficult to effectively treat, particularly in severe cases.

SUMMARY OF THE INVENTION

The present invention provides a method of diagnosing the likelihood of autism in patients, and particularly children. Broadly speaking, the diagnostic method of the invention involves first obtaining from a patient a sample of a body fluid selected from the group consisting of urine, blood, saliva and cerebral spinal fluid. Such a sample is then analyzed to determine the quantity therein of at least one marker compound selected from the group consisting of citramalic acid, 5-hydroxy-methyl-2-furoic acid, 3-oxo-glutaric acid, furan-2,5-dicarboxylic acid, tartaric acid, furancarbonylglycine, arabinose, dihydroxyphenylpropionic acid, carboxycitric acid and phenylcarboxylic acid. Such marker compounds may inhibit normal Krebs cycle function.

In any case, once the quantities of one or more of the marker compounds are determined in the body fluid sample, these quantities are compared with normal quantities of the corresponding compounds found in the same type of body fluid sample in non-autistic individuals of approximately the same age as the patient in question. In this connection, a sufficient sampling of the respective body fluid type of normal individuals should be obtained so as to achieve statistical significance. Likewise, as used herein, a marker compound is generally deemed to be "abnormally high" when it is at least about two standard deviations greater than the mean of the statistically significant sampling of normal individuals for the marker compound in question. For example, if the body fluid being analyzed is urine, the mean of a given marker compound is determined from the analysis of urine samples from a statically significant sampling of non-autistic individuals. This is used as the standard or "normal" level for the given marker compound, and "abnormally high" amounts of the marker compound would generally be at least about two standard deviations greater than this mean value.

With particular reference to urine samples of children up to about 12 years in age, present data establishes that the respective marker compounds are abnormally high if present in at least one urine sample of a patient in the following amounts:

(a) at least about 10 mmol citramalic acid/mol creatinine in the urine sample;

(b) at least about 100 mmol 5-hydroxy-methyl-2-furoic acid/mol creatinine in the urine sample;

(c) at least about 300 mmol arabinose/mol creatinine in the urine sample;

(d) at least about 100 mmol furan-2,5-dicarboxylic acid/mol creatinine in the urine sample (e) at least about 90 mmol tartaric acid/mol creatinine in the urine sample;

(f) at least about 100 mmol furancarbonylglycine/mol creatinine in the urine sample;

(g) at least about 1 mmol 3-oxo-glutaric acid/mol creatinine in the urine sample;

(h) at least about 250 mmol dihydroxyphenylpropionic acid/mol creatinine in the urine sample;

(i) at least about 50 mmol carboxycitric acid/mol creatinine in the urine sample; and (j) at least about 100 mmol phenylcarboxylic acid/mol creatinine in the urine sample.

In actual practice, the diagnostic test of the invention is preferably carried out by analyzing urine samples of a patient for a plurality, and preferably all, of the marker compounds. It may be that in certain instances a given individual's urine will be abnormally high in a number of the compounds, but not all. Therefore, quantitation of all of the marker compounds and comparison with the mean normals is preferred. Likewise, the urine samples should be collected over a period of time, e.g., on a daily basis over a period of at least seven days.

The invention also relates to a method of treating an autistic patient in order to ameliorate certain symptoms of autism. Such method comprises the step of administering an antifungal drug to the patient. Although not essential, such drugs are generally administered orally. A preferred antifungal drug mycostatin may be employed, and is preferably given at a level of at least about 200,000 units per day for a period of at least seven days.

DETAILED DESCRIPTION OF THE PREFERRED EMBODIMENT

Figure 1:
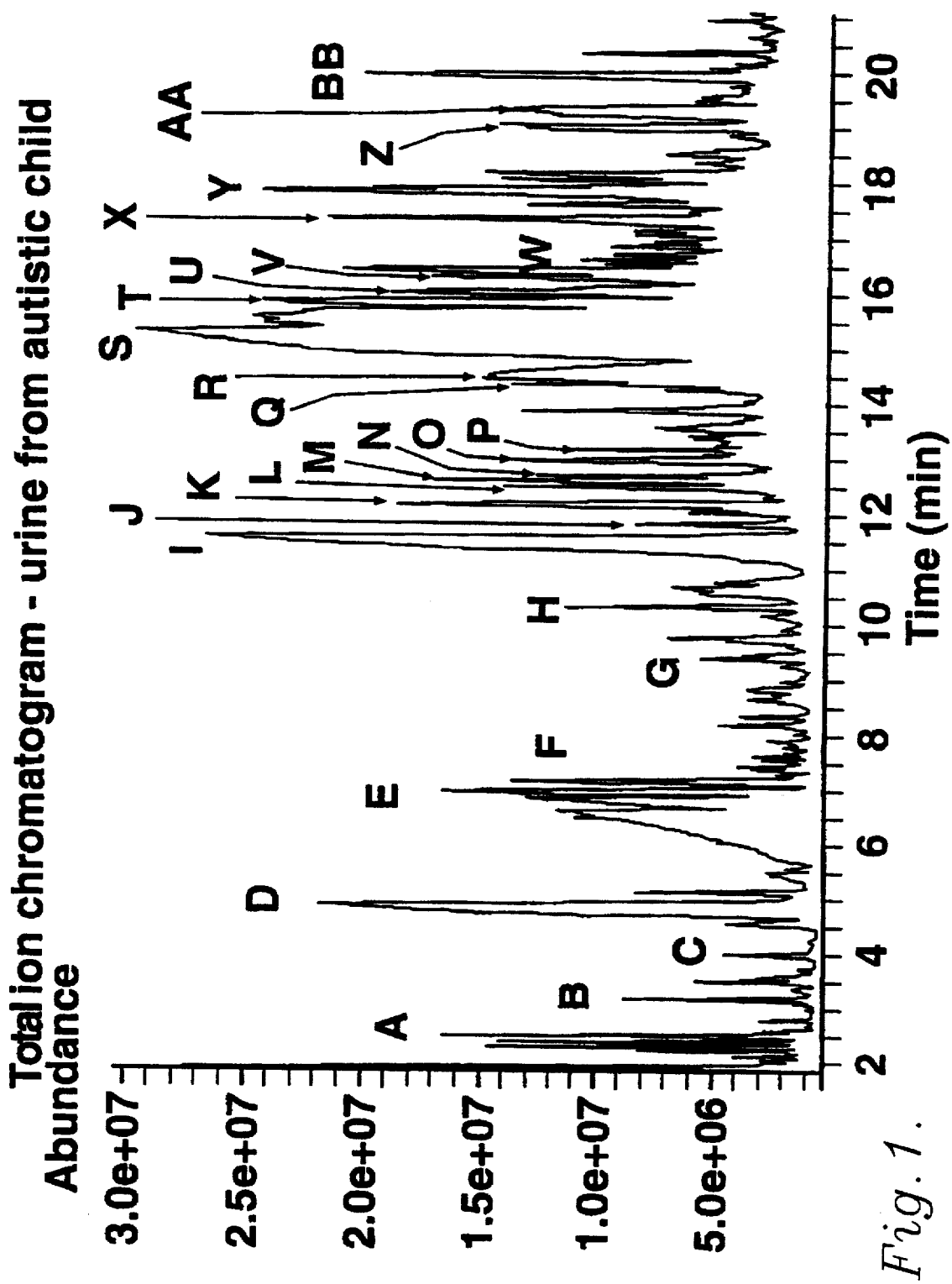
FIG. 1 is a gas chromatography-mass spectrometry (GC/MS) chromatogram obtained from an analysis of a urine sample of an autistic child and illustrating the concentrations of various trimethylsilyl (TMS) derivative compounds wherein the peaks are identified as follows: A, glycollic acid; B, oxalic acid; C, 3-hydroxyisobutyric acid; D, urea; E, phosphoric acid; F, succinic acid; G, deoxytetronic acid; H, citramalic acid; I, undecanoic acid (internal standard); J, unidentified; K, 3-hydroxyphenylacetic acid; L, 2-oxoglutaric acid; M, 4-hydroxyphenylacetic acid; N, furandicarboxylic acid; O, furancarbonylglycine; P, tartaric acid; Q, arabinose; R, aconitic acid; S, hippuric acid; T, citric acid; U, dihydroxyphenylpropionic acid; V, vanillylmandelic acid; W, 3-indoleacetic acid; X, ascorbic acid; Y, citric acid analog; Z, uric acid; AA, unidentified; BB, 4-hydroxyhippuric acid.

The following examples describe the diagnosis and treatment techniques in accordance with the invention. It is be understood that these examples are set forth by way of illustration only, and nothing therein shall be taken as a limitation upon the overall scope of the invention. The attached list of references are referred to by number in the Examples and are incorporated by reference herein.

Example 1

Summary

In this example, the urine of two brothers (A and B) with autistic features were analyzed for the presence of elevated amounts of abnormal Krebs cycle metabolites. These metabolites included citramalic, tartaric (3-OH-malic), and 3-oxoglutaric acids, and compounds tentatively identified as a citric acid analog and partially identified as a phenylcarboxylic acid by the fragmentation pattern of the trimethylsilyl (TMS) derivatives of the compounds and mass shifts of the same compounds derivatized with perdeuterated N,O-bis (trimethylsilyl) trifluoroacetamide. It was discovered that the urine of the autistic brothers exhibited elevated levels of these abnormal metabolites.

Materials and Methods

Gas Chromatography-Mass Spectrometry (GC/MS). Urinary organic acids were quantified as their trimethylsilyl (TMS) ethers or esters essentially as described by Tanaka et al (6). That is, organic acids in urine which are ketocompounds are first converted to ethoxylamine (EO) derivatives and then the urine is acidified to convert the organic acids to an uncharged form more readily extracted from urine into ethylacetate and ether. The solvents are evaporated under nitrogen and then the organic acid residues are reacted with N,O-bis(trimethylsilyl) acetamide (BSTFA) in combination with 1% trimethylchlorosilane. Alcohol, acid and sulfhydryl substituents on the organic acids form trimethylsilyl ethers and esters which are commonly termed TMS derivatives. The byproducts of the reaction, monotrimethyl-silyl trifluoroacetamide and trifluoroacetamide, elute with the solvent front. The solution of TMS derivatives is injected into the GC/MS and the organic acids are identified by comparison to a GC/MS library of known compounds.

In each case, 1 mL of urine was incubated with 200 µL of ethoxylamine hydrochloride solution at a concentration of 75 g/L at 60° C. for 30 min. to convert ketoacids to their ethoxime derivatives (7). In order to identify unknown compounds, the same procedure was performed except that perdeuterated BSTFA was substituted for ordinary BSTFA. In one experiment methoxylamine at the same concentration as ethoxylamine was substituted in the standard procedure. After the EO conversion, 3 drops of 6 N HCl were added to each sample and the pH was checked to insure that it was 1.0 or below. One hundred µl of undecanoic acid was then added as an internal standard, followed by 3 ml of ethyl acetate. Each sample was then capped and mixed for 1 min., followed by centrifugation for 1 min. The supernatant from each sample was then transferred to another test tube, and 3 ml of ethyl ether was added to the urine residue in the lower layer of the original tube. This original tube was then capped, mixed for 1 min. and centrifuged for 1 min. The supernatant from the first tube after the second centrifugation was then combined with the first supernatant in the second tube. Approximately 2 g of sodium sulfate was then added to the combined supernatants, followed by capping, mixing for 1 min. and centrifugation for 1 min. The supernatant from this step was then decanted into a vial and put in a 37° C. heating block under nitrogen for complete evaporation.

After evaporation, the appropriate amount of BSTFA was added to the evaporated extract based upon urine creatinine concentration (determined from an original aliquot of the urine sample). The following sets forth the amount of BSTFA employed:

| Creatinine Conc. (mg/dL) | µl of BSTFA |
| --- | --- |
| 0–24.9 | 50 |
| 25.0–49.9 | 100 |
| 50.0–74.9 | 150 |
| 75.0–99.9 | 200 |
| 100.0–124.9 | 250 |
| 125.0–149.9 | 300 |
| 150.0–174.9 | 350 |
| 175+ | 400 |

After addition of the BSTFA, the heating block was set to 60–90° C. (average 75° C.) and the BSTFA-supplemented extract was placed in the block for 10 min. Thereafter, the urine vial was removed and allowed to cool. Using a transfer pipette, the patient's BSTFA-supplemented extract was placed into a GC/MS autosampler vial. Such vials were then used in conventional fashion for GC/MS analysis, using the manufacturer's directions and software.

All analytical standards were purchased from Sigma Chemical Co., St. Louis, Mo. Quantitation for compounds for which no analytical standards were available were performed by assigning the response of an average size ion chromatogram peak as 100 units and then calibrating all other peaks against these arbitrary standards. The GC/MS system used was from Hewlett Packard, Palo Alto, Calif. and consisted of an HP5970 mass selective detector, a 5890A gas chromatograph, a model 18593B autosampler, and an Apollo 400 series computer with a 664 MB hard disk drive. The operating software for both instrument control and data analysis was a UNIX-based Chemsystem which operated simultaneously with a Target 2 software system. For GC/MS analysis, 1 µL of sample was injected onto a 15-meter, DB-1 capillary column with a 0.25 mm internal diameter and an 0.25 micron film from J & W Scientific, Folsom, Calif., using purified helium as the carrier gas. All experiments were done using electron-impact (EI) ionization with electron energy of 70 eV. The temperature program was started at 90° C., held for 4 min. after injection and then increased to 280° C. at a rate of 8° C./min. The electron-impact mass spectra of arabinose and arabitol were differentiated by the fact that the spectrum of the TMS derivative of arabitol has a significant ion at m/z 319 that is not present in the spectrum of the TMS derivative of arabinose.

Urine samples were randomly collected in plastic screw-cap containers and stored at −20° C. until tested. Normal urine samples were collected from children of laboratory employees. Urine creatinine tests were performed by a modification of the Jaffe method (8) on a Beckman CX-7 chemistry analyzer using standard Beckman creatinine reagents. The procedures followed were in accordance with the Helsinki Declaration of 1975, as revised in 1983.

Results

Figure 2:
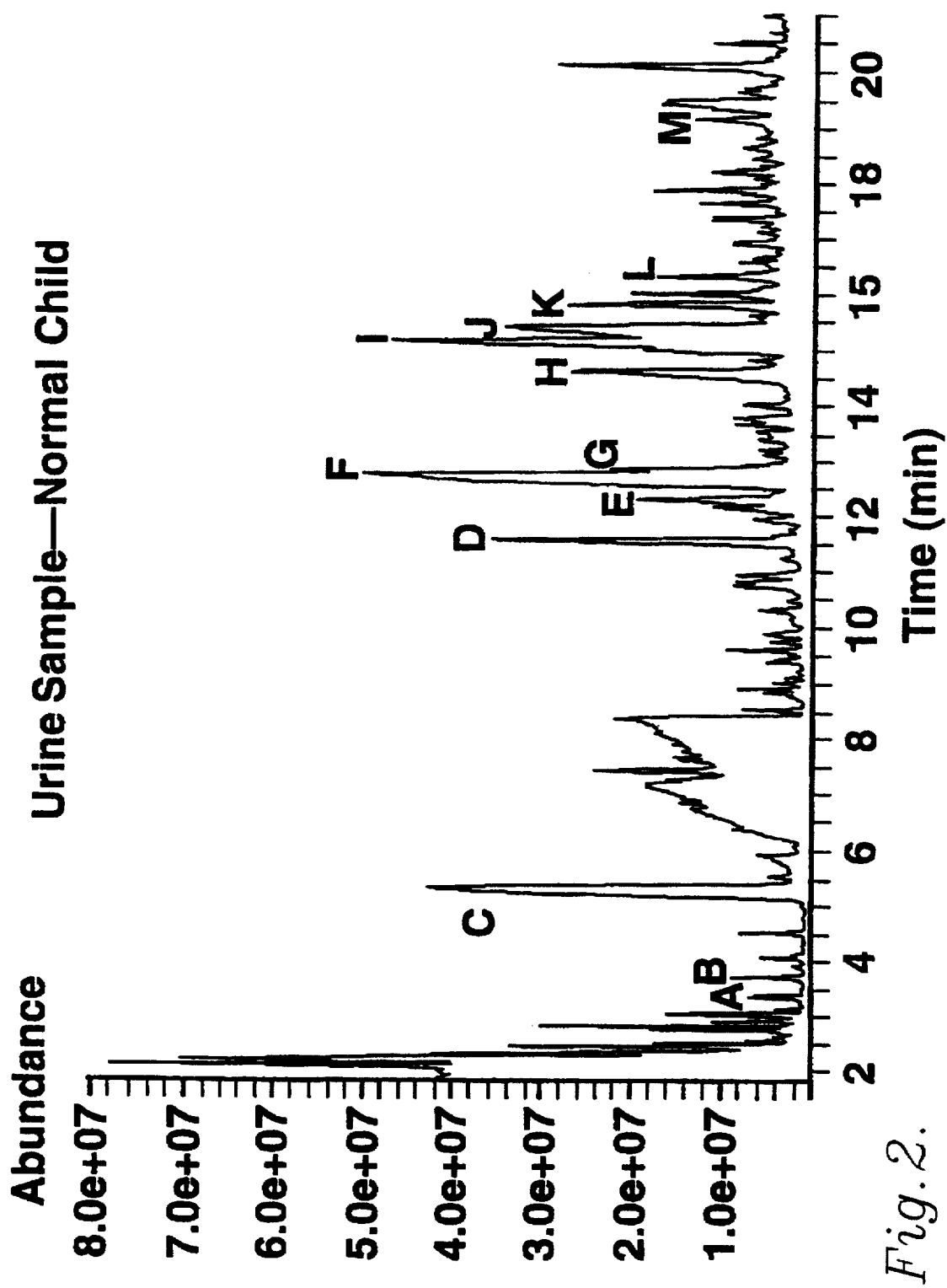
FIG. 2 is a GC/MS chromatogram similar to that of FIG. 1 but illustrating the results using the urine sample of a normal child wherein the TMS derivative peaks are identified as follows: A, pyruvic; B, oxalic; C, urea; D, undecanoic; E, 3-hydroxyphenylacetic; F, 2-oxoglutaric; G, 4-hydroxyphenylacetic; H, aconitic; I,J, hippuric; K, citric; L, vanillylmandelic; and M, 3-hydroxyhippuric.

A typical total ion current (TIC) chromatogram of the TMS derivatives in the urine of brother A is shown in (FIG. 1). Significant peaks at 10.31 min., 14.36 min., 17.78 min., and 18.86 min. were present that were not prominent in normal urine samples (FIG. 2). The results of the urine samples of brother B were very similar to those of his sibling A. In addition, tartaric acid was frequently found in high concentrations in urine samples of these siblings. A much smaller peak at 12.1 min. was also detected in some of the urine samples of the siblings with autistic features. Since the concentration of these metabolites in urine samples of the siblings vary widely, it is important to show data demonstrating the variability of the concentration of these compounds and comparing these concentrations to those in normal children. Therefore, results for four of the metabolites are presented in an identification section and a quantitation section comparing them to normals. No identification section is given for tartaric acid since it is well-recognized in the field of metabolic diseases. No quantitation section is given for 3-oxoglutaric acid since it was only quantitated in some of the samples.

Figure 3:
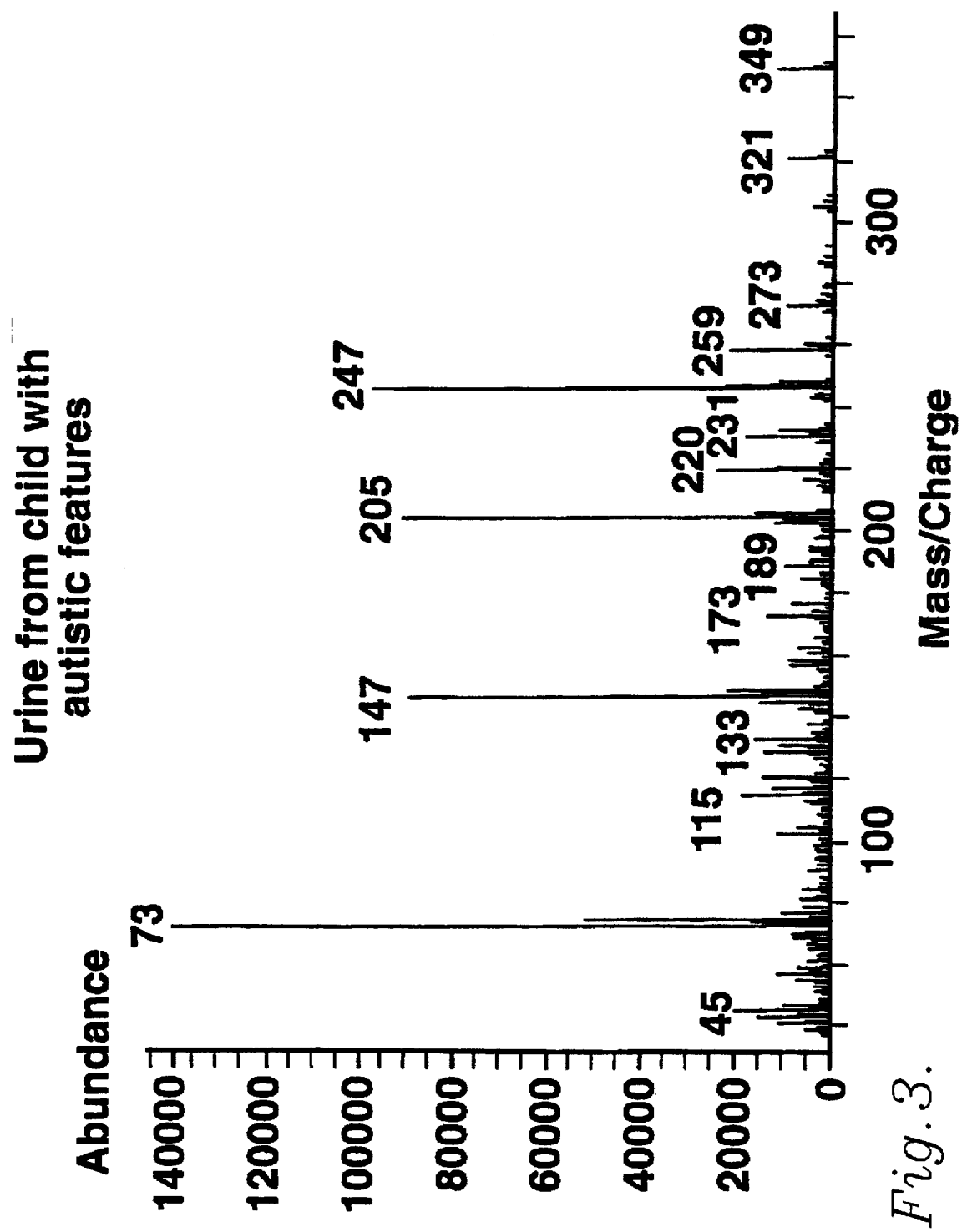
FIG. 3 is a GC/MS chromatogram giving the mass spectrum of a compound identified as the TMS derivative of 3-methyimalic acid found in the urine of an autistic patient, wherein the numbers within the graph represent the mass in Da of the ion fragments of the compound.
Figure 4:
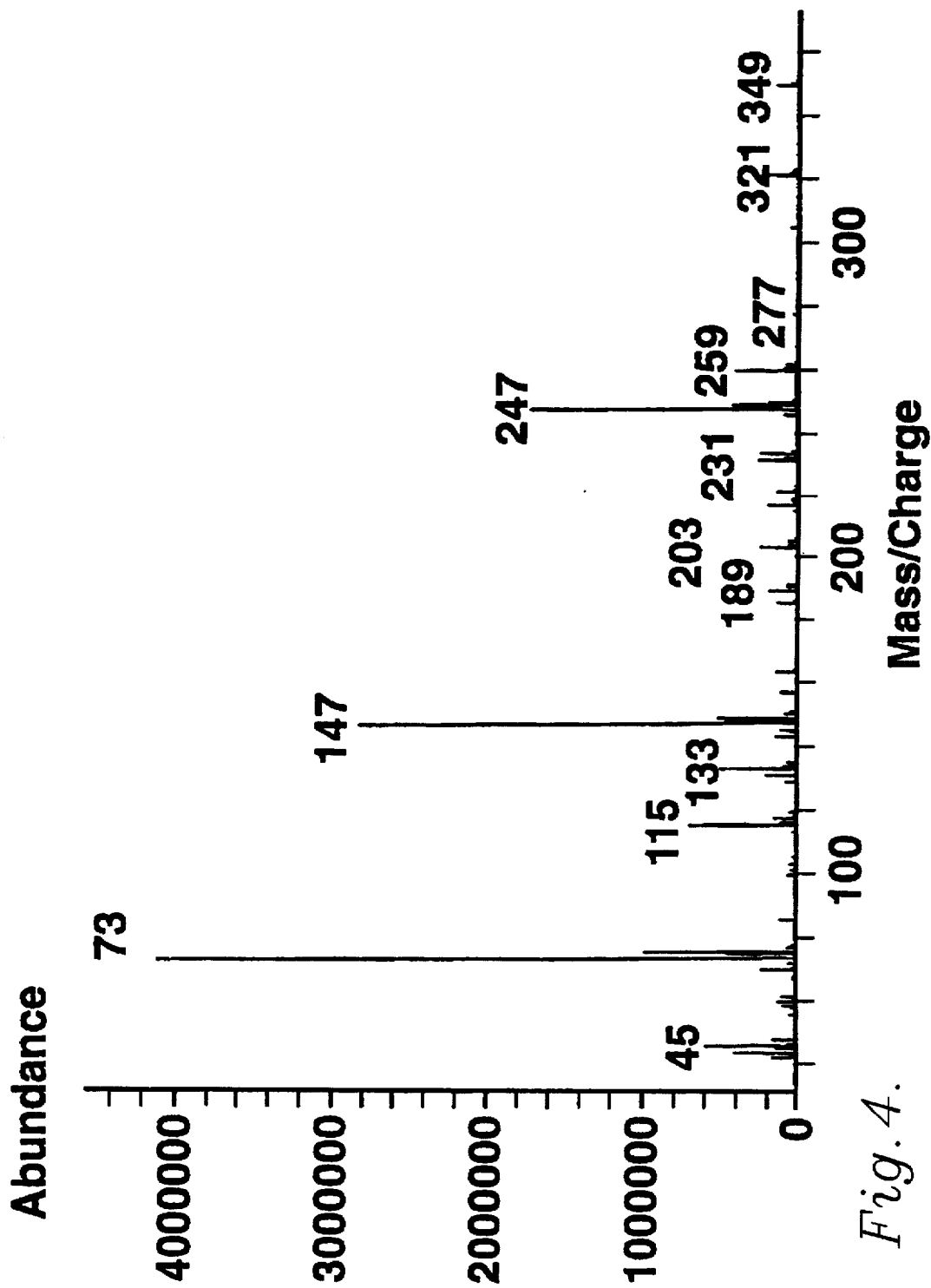
FIG. 4 is a GC/MS chromatogram giving the mass spectrum of the TMS derivative of authentic citramalic acid.
Figure 5:
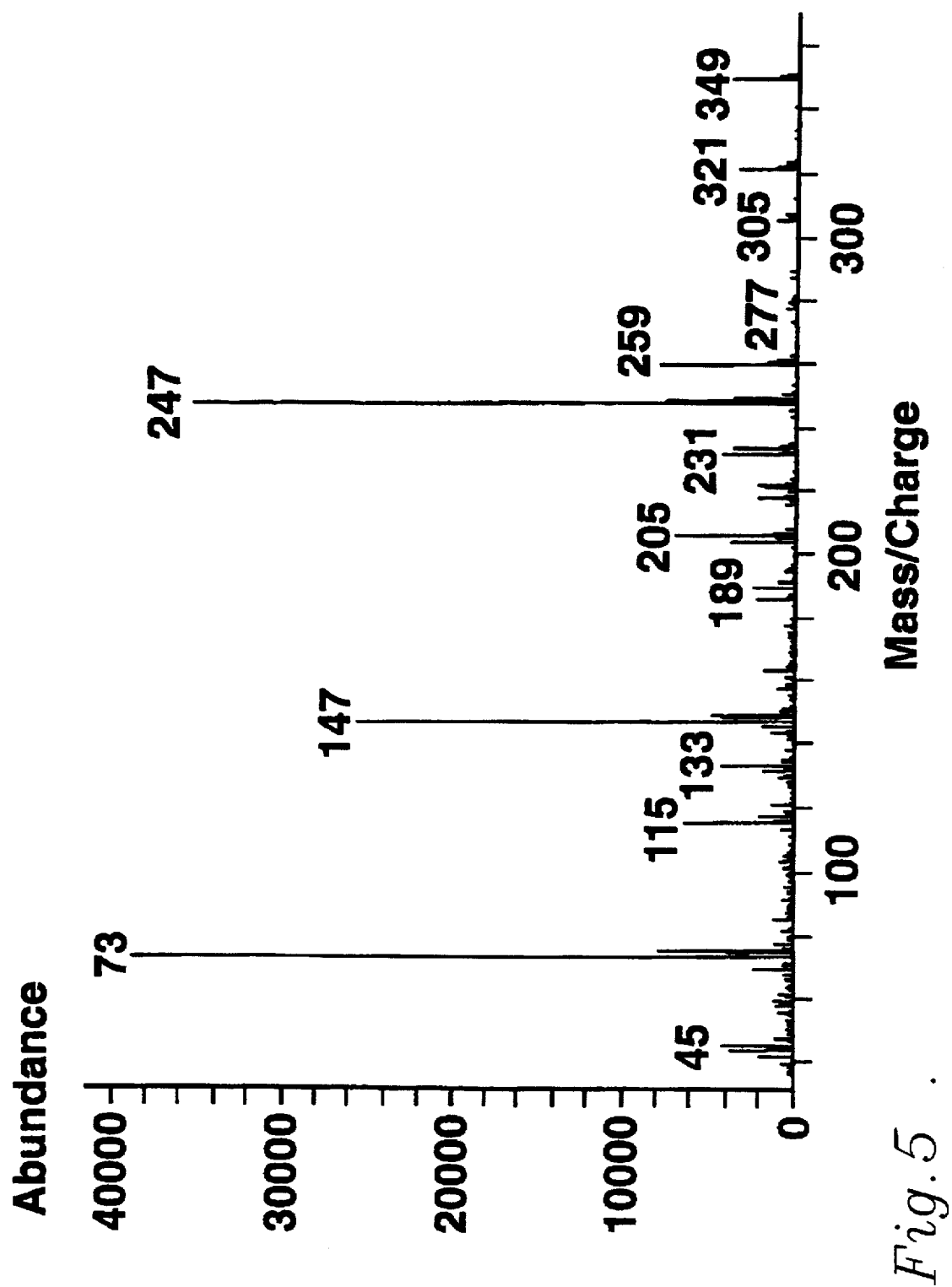
FIG. 5 is a GC/MS chromatogram giving the mass spectrum of a compound found in the urine of an autistic patient and which by comparison with the chromatogram of FIG. 4 is identified as citramalic acid TMS derivative.
Figure 6:
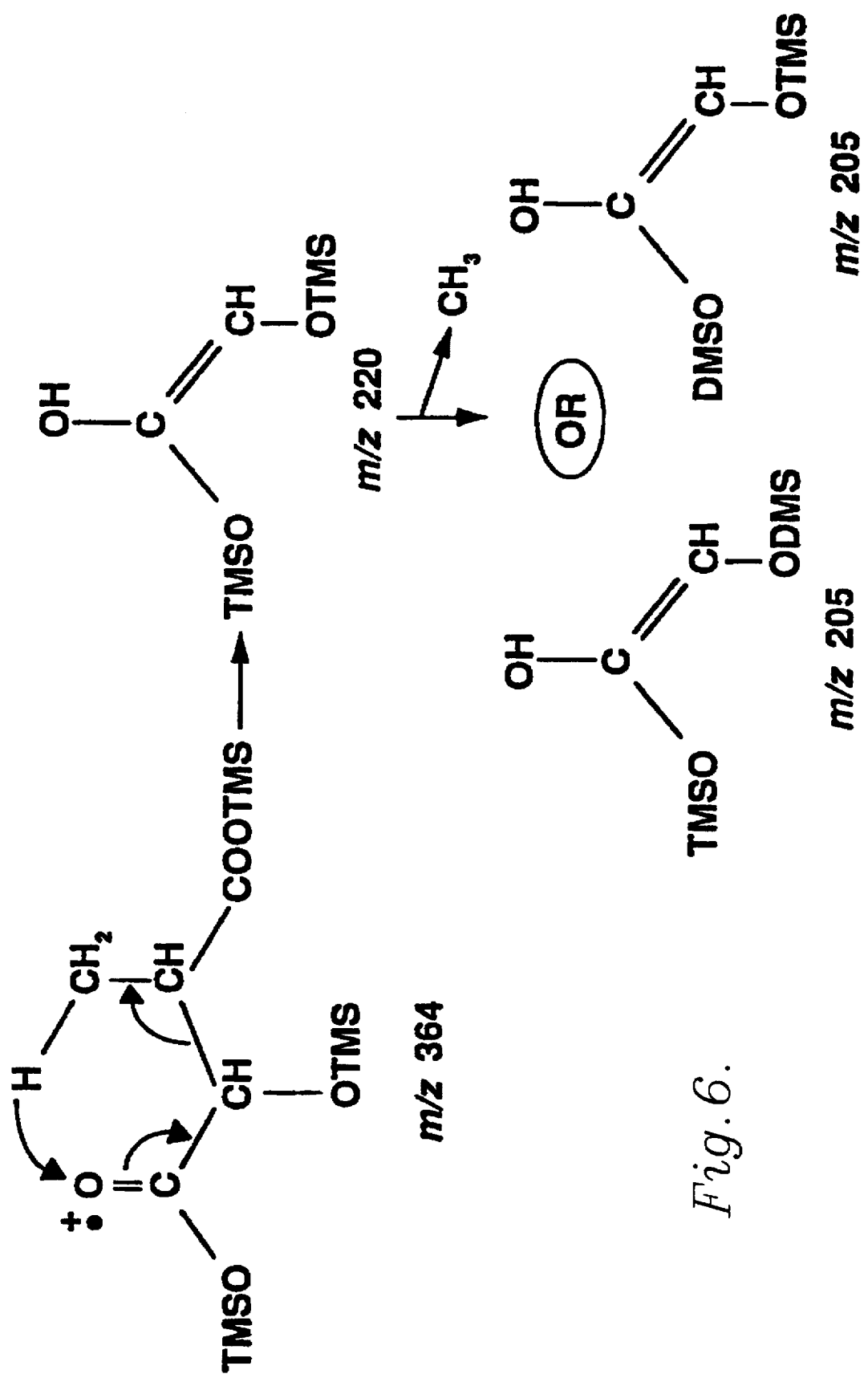
FIG. 6 illustrates a possible mechanism for the formation of the ion fragments referred to in FIG. 3.

Tentative identification of 2-methylmalic(citramalic) and 3-methylmalic acids. The mass spectrum of the peak at 10.31 min. (FIG. 3) is very similar to that of authentic citramalic acid (2-hydroxy-2-methylbutanedioic or 2-methyl-malic acid (FIG. 4) and has an identical retention time (±0.1 min.). However, a very abundant ion at m/z 205 and a less abundant ion at m/z 220 were present in the spectrum of the peak in the urine of the child with autistic features. The abundance of the ions at m/z 205 and m/z 220 varied widely in different urine samples of the brothers with autistic features. For example, in a spectrum from a different urine extract the abundances of the ions at m/z 203 and 205 are approximately equal and the 220 ion is not detectable (FIG. 5). It is believed that the compound producing the 205 and 220 ions is 2-hydroxy-3-methyl-butanedioc (3-methylmalic). The abundant ion fragment at m/z 220 would be consistent with the loss of a $CH_3$—C—$CO_2TMS$ fragment following a McLafferty rearrangement and cleavage of the bond between carbons 2 and 3; a loss of $CH_3$ from another TMS group from the m/z 220 ion fragment yields the ion fragment at m/z 205 (FIG. 6). Equivalent ion fragments cannot be formed by fragmentation of 2-methylmalic. 3-Methylmalic acid is not commercially available for confirmation studies.

Figure 7:
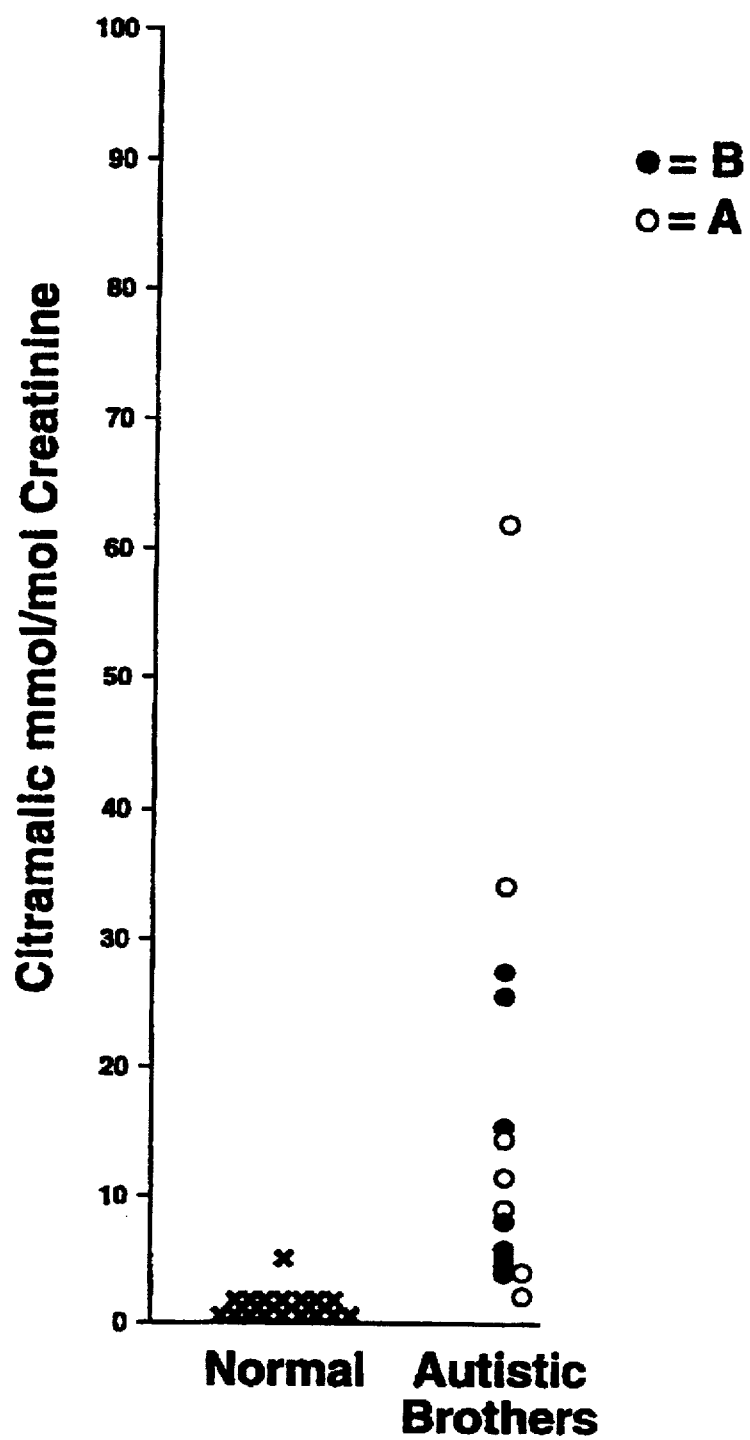
FIG. 7 is a comparative graph depicting the amounts of the TMS derivative of citramalic acid in normal patients and the autistic brothers described in Example 1.

Quantitation of Methylmalic Acids. For the quantitative studies, the ion signal peak at m/z 247 was used for quantitation. Since both 2- and 3-methylmalic acid isomers have abundant 247 ions and we used citramalic acid (2-methylmalic) as the calibration standard, the values we give for citramalic acid probably represent the total of these isomers. Concentrations of this compound are markedly higher in the brothers with autistic features than in normal children. Citramalic acid concentrations in 19 of the 20 urines from normal children are below 2 mmol/mol creatinine while citramalic acid concentrations in 14 of the 15 urines from the brothers with autistic features exceed 2 mmol/mol creatinine and in one of the urine samples from brother A is 62 mmol/mol creatinine (FIG. 7). The mean citramalic acid concentration in the brothers with autistic features is 14.4 mmol/mol creatinine and 1.5 mmol/mol creatinine in the normal children. The means are statistically different using the t-test at the 0.01 probability level.

Figure 8:
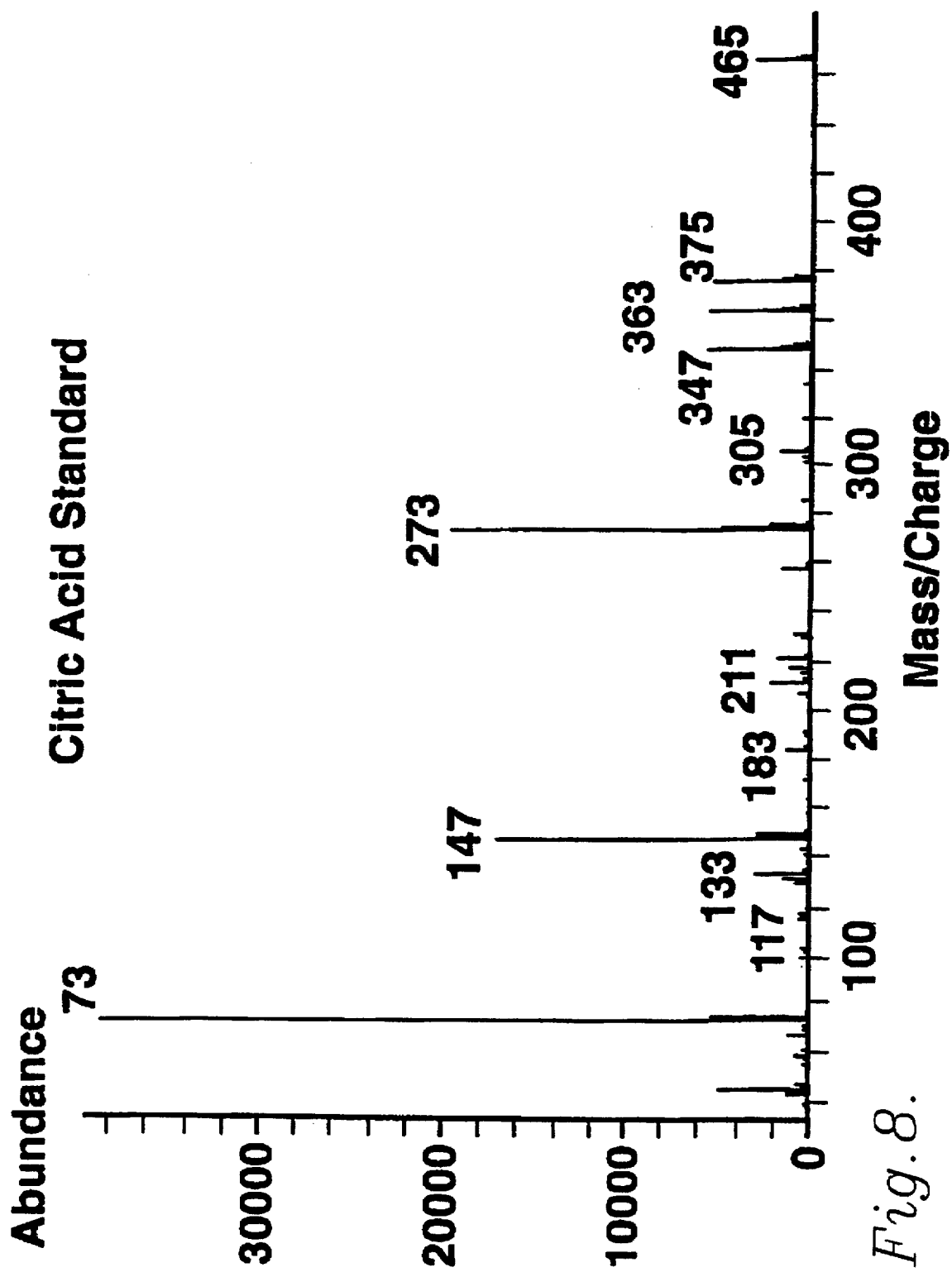
FIG. 8 is a GC/MS chromatogram giving the mass spectrum of citric acid TMS derivative.
Figure 9:
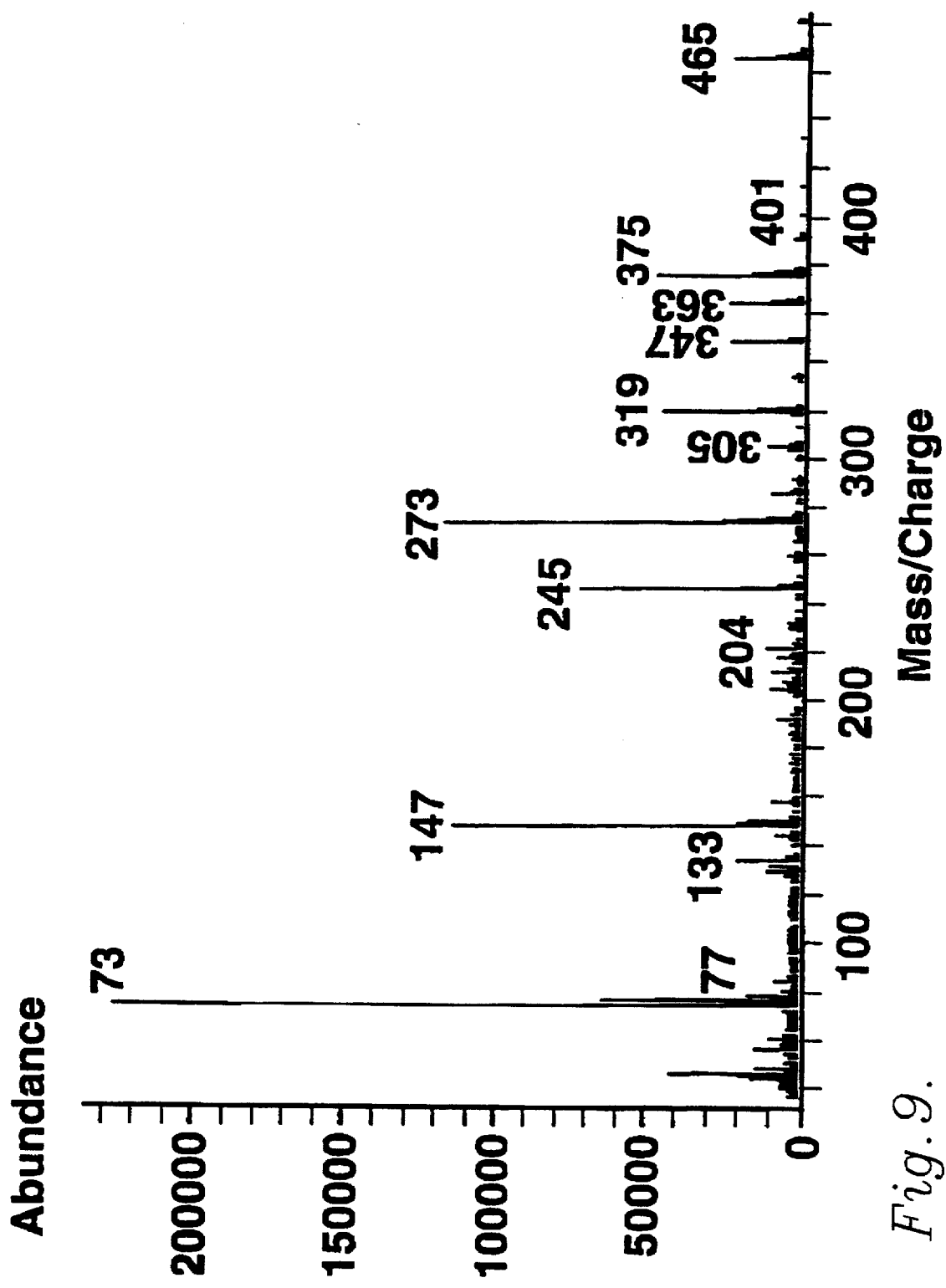
FIG. 9 is a GC/MS chromatogram giving the mass spectrum of isocitric acid TMS derivative.
Figure 11:
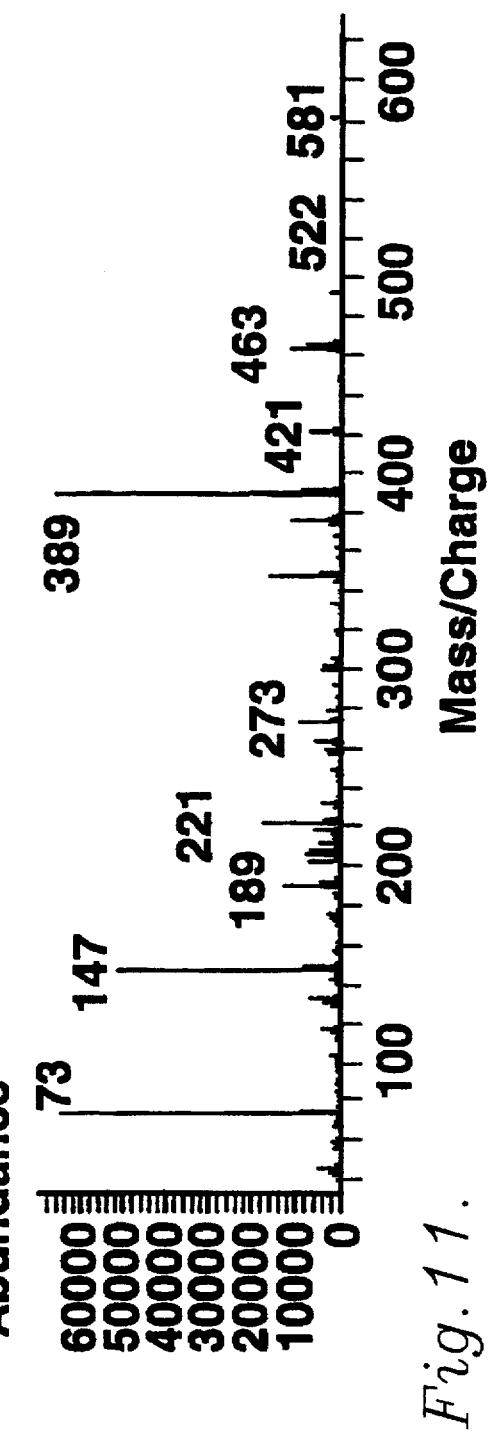
FIG. 11 is a GC/MS chromatogram giving the mass spectrum of the non-perdeuterated TMS derivative referred to in FIG. 10.

Tentative Identification of new citric acid analog. The possibility that a new citric acid analog might be present in the urine of autistic children was considered when an analysis of the mass spectrum of the peak eluting at 7.78 min. (FIG. 11) following the computerized mass spectra library search revealed that the unknown shared several unique ions with the TMS derivatives of citric and isocitric acids (FIGS. 8 and 9) including those for m/z 273, 347, and 375. Selected ion chromatograms of multiple urine extracts revealed that all of these three ions were found only in peaks corresponding to the TMS derivatives of citric, isocitric, and the unknown peak. The unknown spectra had a significant ion at m/z 581. Since the largest detectable ion for TMS derivatives is frequently the M-15 ion due to the loss of a methyl group from one of the TMS groups, the tentative molecular weight of 596 could correspond to a citric acid TMS derivative (molecular weight=480 Da) with an additional COOTMS group (mass=117 Da)–H (mass=1 Da).

Figure 10:
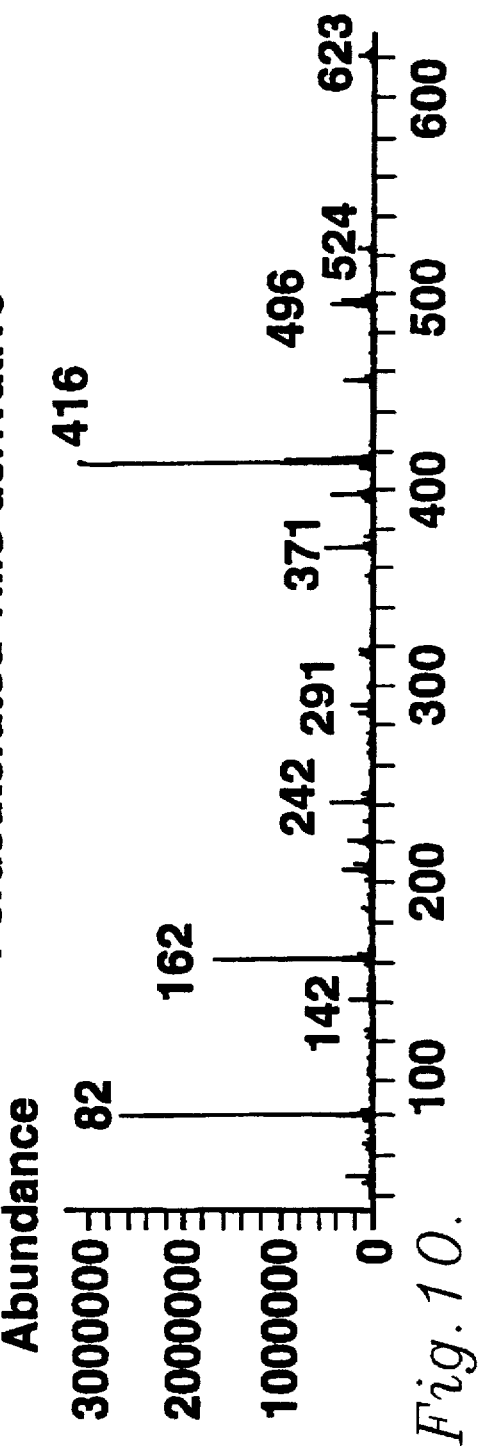
FIG. 10 is a GC/MS chromatogram giving the mass spectrum of the perdeuterated TMS derivative of a citric acid analog.

Additional evidence for a citric acid analog was obtained by making a perdeuterated TMS derivative of the compound. An aliquot of the same urine was extracted by the regular method and then derivatized with perdeuterated BSTFA to identify the fragments, mass losses from the molecular ion, TMS and/or dimethylsilyl (DMS) content of each mass fragment and the number of functional groups. The mass spectra of the compound formed with the perdeuterated BSTFA is given in FIG. 10 and an interpretation of the data from the spectra of both the perdeuterated and nondeuterated BSTFA derivatives are given in Table 1 below.

TABLE 1

| Mass loss from 596 | Major ions with plain TMS | Major ions $d_2$ TMS | Λ | TMS Content | Interpretation |
|---|---|---|---|---|---|
| 523 | 73 | 82 | 9 | 1 TMS | TMS |
| 449 | 147 | 162 | 15 | 1 TMS 1 DMS | TMS—O—DMS |
| 407 | 189 | ? | ? | ? | ? |
| 375 | 221 | 242 | 21 | 2 DMS 1 TMS | ? |
| 323 | 273 | 291 | 18 | 2 TMS | M—COOTMS—COOHTMS—TMSOH |
| 249 | 347 | 371 | 24 | 2 TMS 1 DMS | M—$CH_3$—2COOTMS |
| 221 | 375 | 399 | 24 | 2 TMS 1 DMS | M—$CH_3$—COOTMS—OTMS |
| 207 | 389 | 416 | 27 | 3 TMS | M—COOTMS—TMSOH |
| 175 | 421 | 457 | 36 | 4 TMS | M—$CH_2$COOTMS—CO |
| 133 | 463 | 496 | 33 | 3 TMS 1 DMS | M—$CH_3$—COOHTMS |
| 105 | 491 | 524 | 33 | 3 TMS 1 DMS | M—$CH_2$—TMSOH |
| 15 | 581 | 623 | 42 | 4 TMS 1 DMS | M—$CH_3$ |

The largest mass fragment in the spectrum of the nondeuterated compound is m/z 581 Da; the largest mass fragment in the perdeuterated derivative is m/z 623, a shift of 42 Da. This mass shift is consistent with the 581 Da fragment ion containing five derivatized functional groups, four of which are TMS and one of which is DMS. These data also indicate that the m/z 581 ion is the M-15 ion, and that the molecular weight of the penta TMS derivative is 596 Da. The ion at m/z 491 in the spectrum of the nondeuterated compound corresponds to the ion at m/z 524 in the spectrum of the perdeuterated derivative, a shift of 33 Da, indicating that this ion contains three TMS and one DMS groups, and that one TMS group and a methyl group from one TMS group were lost from the molecular ion in the formation of this ion. This ion at m/z 491 results from a loss of 105 Da from the molecular ion; one TMS accounts for 73 Da and the methyl group accounts for 15 Da, leaving a mass of 17 Da unaccounted. This remaining mass of 17 Da is consistent with the loss of OH, as TMSOH, an extremely common loss in the literature of the mass spectra of TMS derivatives (9).

The ion at m/z 463 in the spectrum of the nondeuterated compound corresponds to the ion at m/z 496 in the spectrum of the perdeuterated derivative, a shift of 33 Da, indicating that this ion contains three TMS and one DMS groups and that one TMS group and a methyl group from another TMS group were lost in the formation of this ion. The ion at m/z 463 results from a loss of 133 Da from the molecular ion; one TMS accounts for 73 Da and the methyl group from another TMS accounts for 15 Da, leaving a mass of 45 Da unaccounted, which clearly is consistent with the loss of COOH, as TMSCOOH, an extremely common loss in the literature of the mass spectra of TMS derivatives (9).

Figure 12:
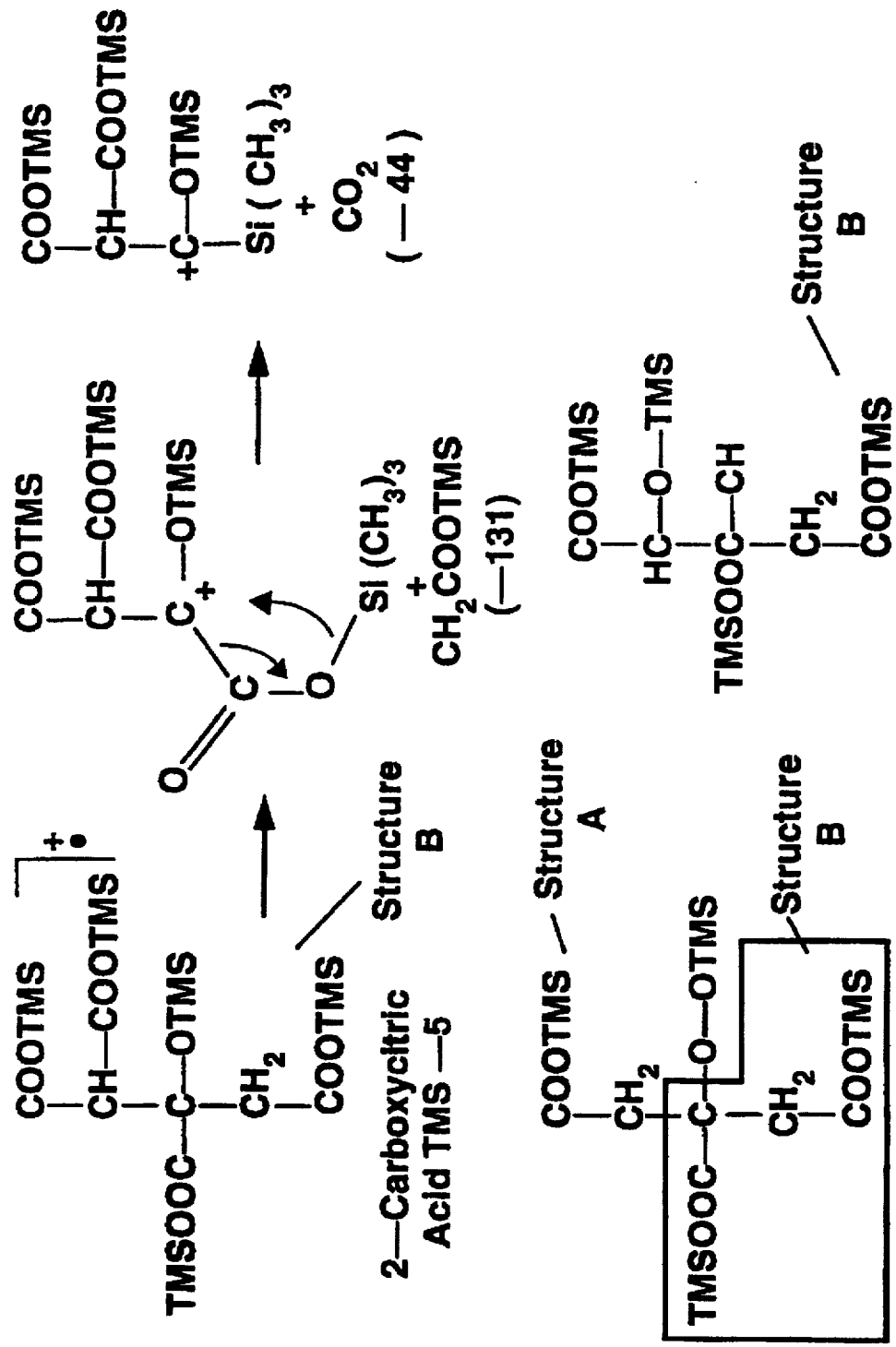
FIG. 12 is a proposed fragmentation mechanism of citric acid, isocitric acid, and citric acid analog derivatives that yield 175 Da losses from the molecular ion.

The ion at m/z 421 in the spectrum of the nondeuterated compound corresponds to the ion at m/z 457 in the spectrum of the perdeuterated derivative, a shift of 36 Da, indicating that this ion contains four TMS groups and that one TMS group was lost in the formation of this ion. The ion at m/z 421 is unusual in that one COO is lost without an accompanying TMS group, a neutral loss of 175 from the molecular ion (FIG. 12 and Table 1). This ion (FIG. 12) is attributed to the loss of $CH_2COOTMS$ (−131) followed by a rearrangement of the COOTMS group attached to carbon-3 in which the silicon atom of this COOTMS group attacks carbon-3 and $CO_2$ is expelled (−44). Similar losses of 175, also found in the mass spectra of citric and isocitric acids, are consistent with the proposition that the structures (FIG. 6) for the three compounds are similar and result in similar fragmentation patterns. This loss of 175 can occur in two different ways in citric acid since structure a and structure b (FIG. 12) are equivalent. In isocitric acid, this loss of 175 can only involve structure b of the molecule. The molecular weight of the unknown compound is 596 Da. The fragmentation pattern and labeling prove the presence of at least one OTMS group and two COOTMS groups, accounting for 323 Da. Two additional TMS groups account for 146 Da. The results of the labeling experiments with the unknown and the similar fragmentation patterns of the unknown, citric acid, and isocitric acid are consistent with identical portions of these molecules labeled structure b in FIG. 12. The carbon atom at C-3 and the $CH_2$ group in structure b in FIG. 12 account for an additional 26 Da, leaving 101 Da unaccounted; the two additional functional groups remaining can only be COOTMS and TMSOH since there are no losses consistent with any other functional groups. Thus, the rest of the molecule contains two COOTMS groups, or two OTMS groups, or one OTMS group and one COOTMS group. The presence of two additional OTMS groups is unlikely because there are no ions that correspond to the loss of two OTMS groups. Thus, the unknown compound is likely a citric acid analog with an extra carboxylic acid group or a hydroxylcitric acid. Because the unknown is more unstable than citric acid, it is believed that a 2-carboxycitric acid structure is more likely. 2-carboxycarboxylic acids are relatively unstable.

Because this derivative was formed in the presence of ethoxylamine HCl, it was desired to rule out the possibility that the compound is an ethoxime derivative. Substitution of methoxylamine HCl in the procedure yielded a derivative with an identical spectrum indicating that no oxime was present in the molecule, and therefore no keto group was present in this compound. Curiously, when an identical urine aliquot was tested with the oxime derivatization step omitted, this compound was not detected. It was suspected that the failure to detect this compound was due to the salt effect of the methoxylamine HCl or ethoxylamine HCl which increased the efficiency of extracting an extremely water-soluble compound with five polar functional groups into the organic solvents.

An attempt was made to confirm this idea by substituting sodium chloride for the oxime reagent and then performing the normal extraction and derivatization procedure. Results of this experiment revealed that this compound was still not detected, indicating that the effect of the oxime is not a simple salting out effect but might be the result of ion pair formation between the positively charged oxime ions and the negatively charged citric acid analog. It was also noted that the size of the peak for citric acid was also markedly diminished when oxime reagents were omitted also strengthening the hypothesis that the oxime reagent acts as an ion pair extraction reagent for other highly water-soluble acids. However, 2- carboxycarboxylic acids are very unstable, especially in acidic solution and tend to decarboxylate and the oxime might also protect this molecule from decarboxylation.

Figure 13:
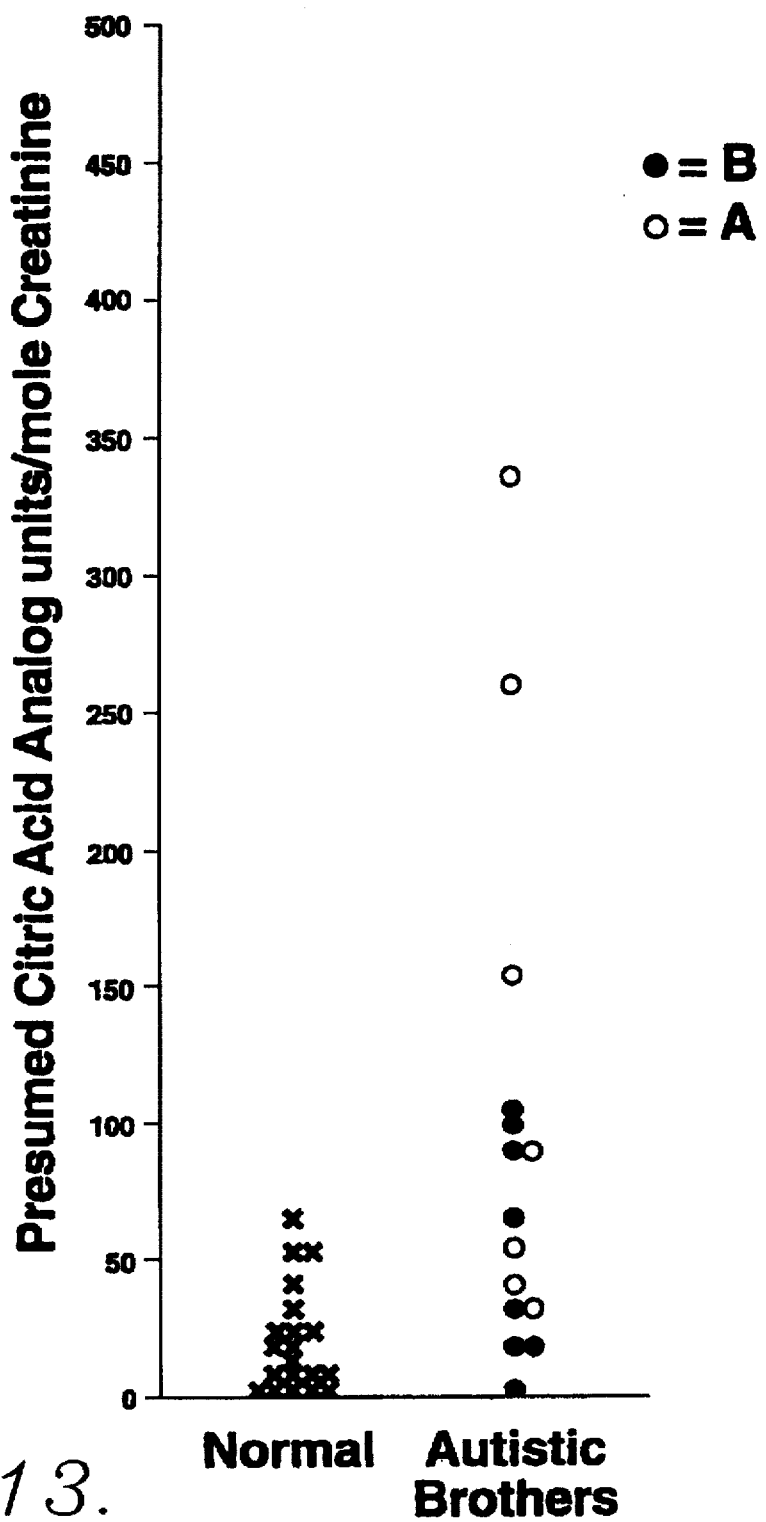
FIG. 13 is a comparative graph depicting the amounts of the TMS derivative of the citric acid analog referred to in FIG. 11 in normal patients and the autistic brothers referred to in Example 1.

Quantitation of tentatively identified citric acid analog. The tentatively identified citric acid analog is found in much higher values in the urine of the brothers with autistio features compared to normal children (FIG. 13). The mean value for the brothers with autistic features is 93 units/mol creatinine while the mean value for normal children is 18 units/mol creatinine. Brother A excreted the largest amount of (335 units/mol creatinine). If this compound has a response factor for total ion current equivalent to citric acid, the absolute concentration would be 137 mmol/mol creatinine. The presence of this compound in the urine of 18/20 normal children was confirmed by identification with complete mass spectra demonstrating that this compound is not a drug metabolite.

Figure 14:
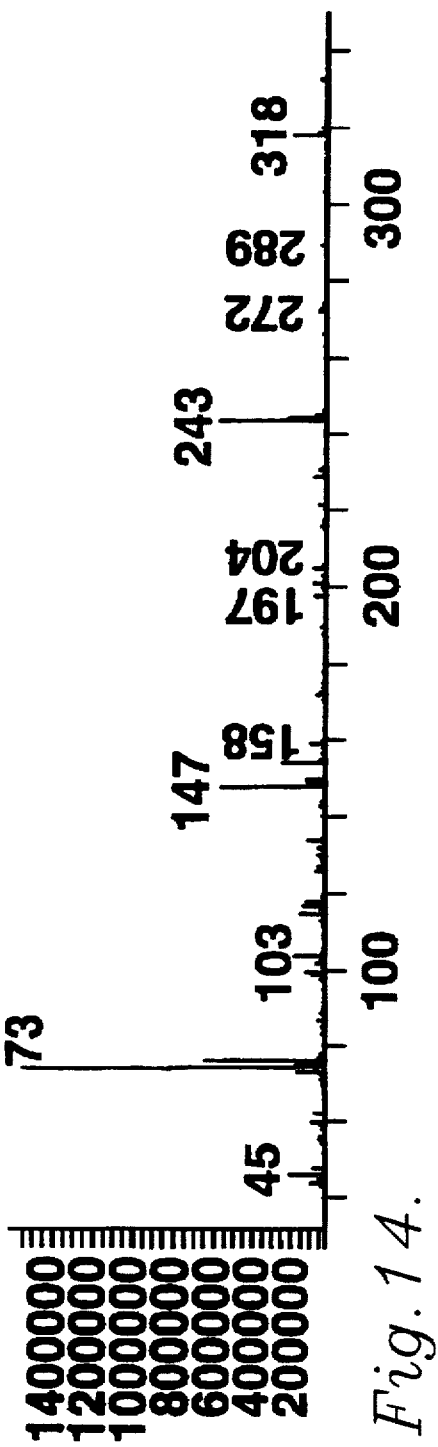
FIG. 14 is a GC/MS chromatogram giving the mass spectrum of 3-oxo-glutaric acid TMS derivative from the urine of an autistic child.
Figure 15:
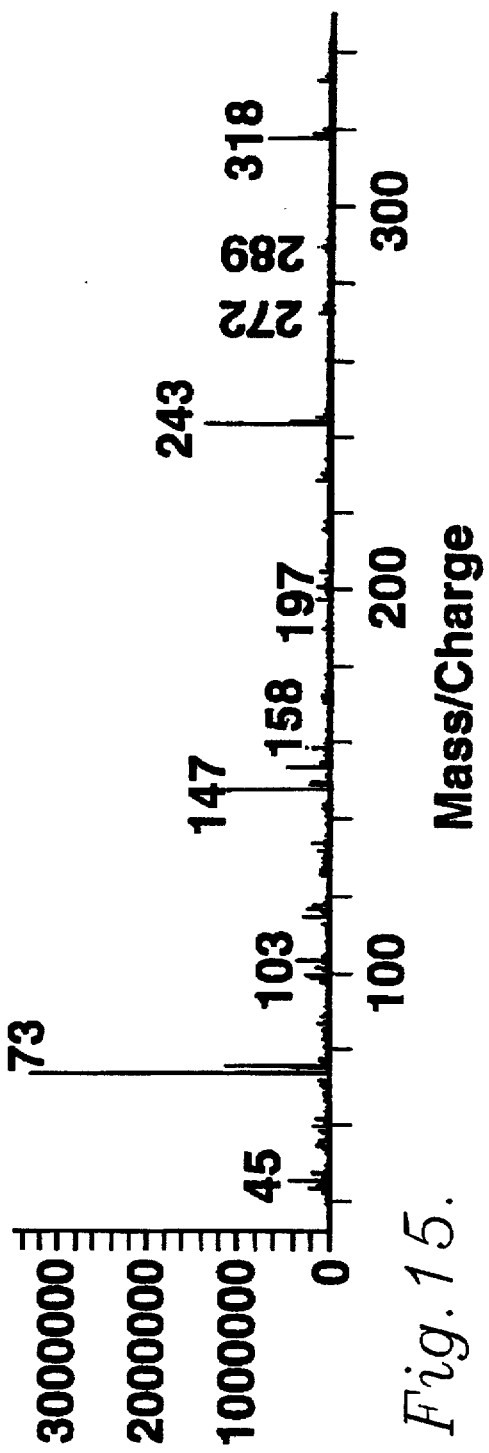
FIG. 15 is a GC/MS chromatogram giving the mass spectrum of the TMS derivative of authentic 3-oxoglutaric acid.
Figure 16:
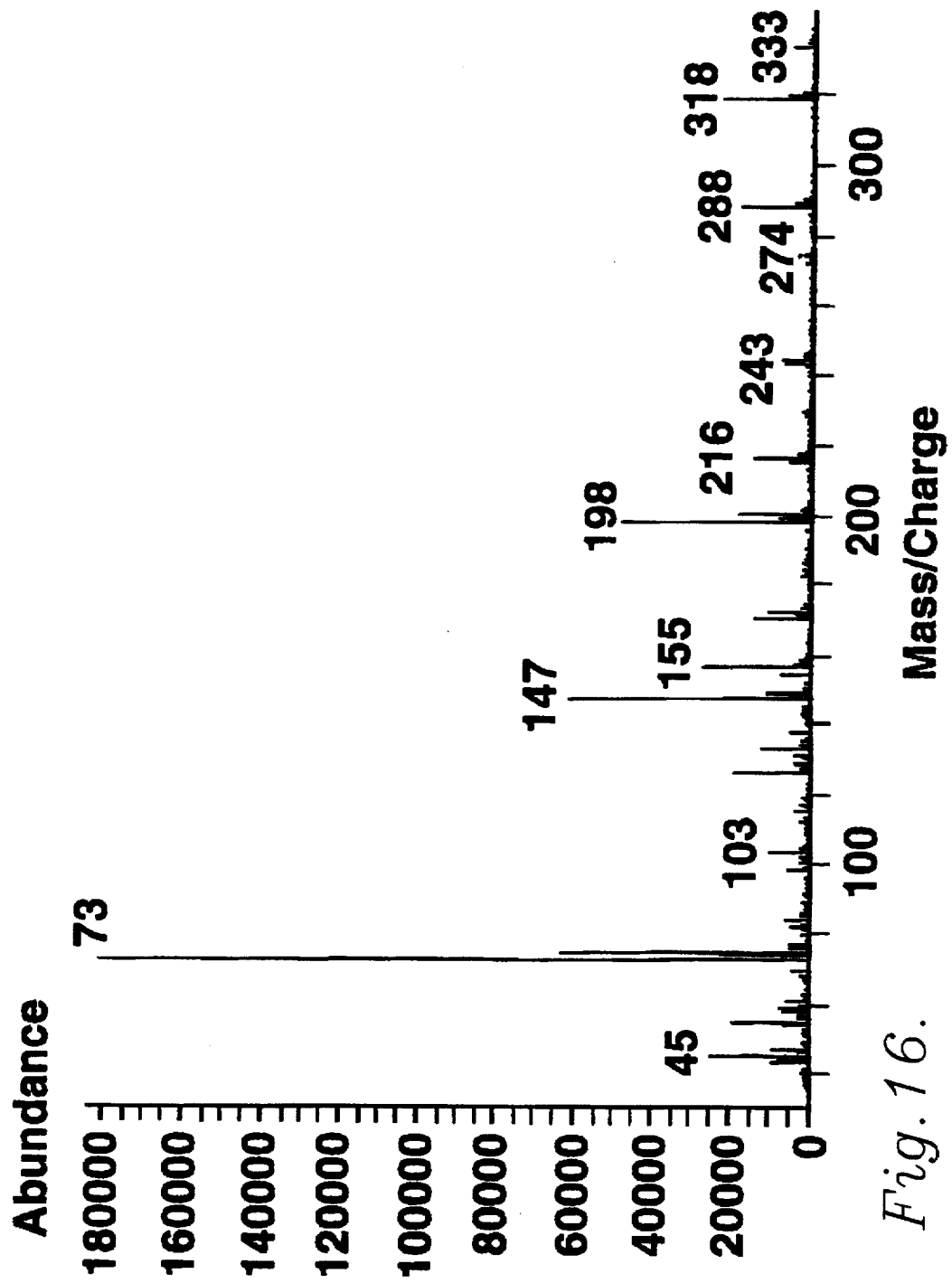
FIG. 16 is a GC/MS chromatogram giving the mass spectrum of the TMS derivative of 3-oxoglutaric acid.

Identification of 3-oxoglutaric acid. 3-Oxoglutaric acid in the urine of these brothers was identified by the fact that the retention time of the peak at 12.1 min. by GC/MS and the spectrum of the ethoxylamine-TMS derivative were similar to that of authentic 3-oxoglutaric acid processed by the standard method. In addition, the ion ratio for masses 318/243 is characteristic of 3-oxoglutaric acid. The ion ratio for 2-oxoglutaric acid is markedly different. However, the concentration of this compound was too low to obtain a conclusive mass spectrum. The urine samples of the brothers were also unusual in that the concentration of 3-oxoglutaric acid was nearly as great as that of 2-oxoglutaric acid, a finding confirmed in other autistic children. The urine of another unrelated autistic child had a higher concentration of this compound which permitted unequivocal identification of this compound (FIG. 14). 3-Oxoglutaric acid elutes 0.3 min. before 2-oxoglutaric acid with our chromatographic conditions. The mass spectrum of this compound is consistent with the presence of a di-TMS ethoxylamine derivative. Mass spectra for the two compounds are very similar. Both contain significant ions at m/z 318 due to loss of a methyl group from the molecular ion and significant ions at m/z 103 and 318. The spectrum of the 2-oxoglutaric acid derivative has prominent ions at m/z 288 and 198 (FIG. 16) that are not significant in the spectrum of the 3-oxoglutaric acid derivative (FIG. 15). The fragment at m/z 243 is abundant in the spectrum of 3-oxoglutaric acid but very weak in the spectrum of 2-oxoglutaric. A weak molecular ion at m/z 333 was identified in the spectra of both compounds. 3-Oxoglutaric acid was variably present in the urine of these brothers and was present as a relatively small peak that might not be detected without the use of reconstructed ion chromatograms for m/z 243. The concentration in the child with the highest value was 26 mmol/mol creatinine.

Figure 17:
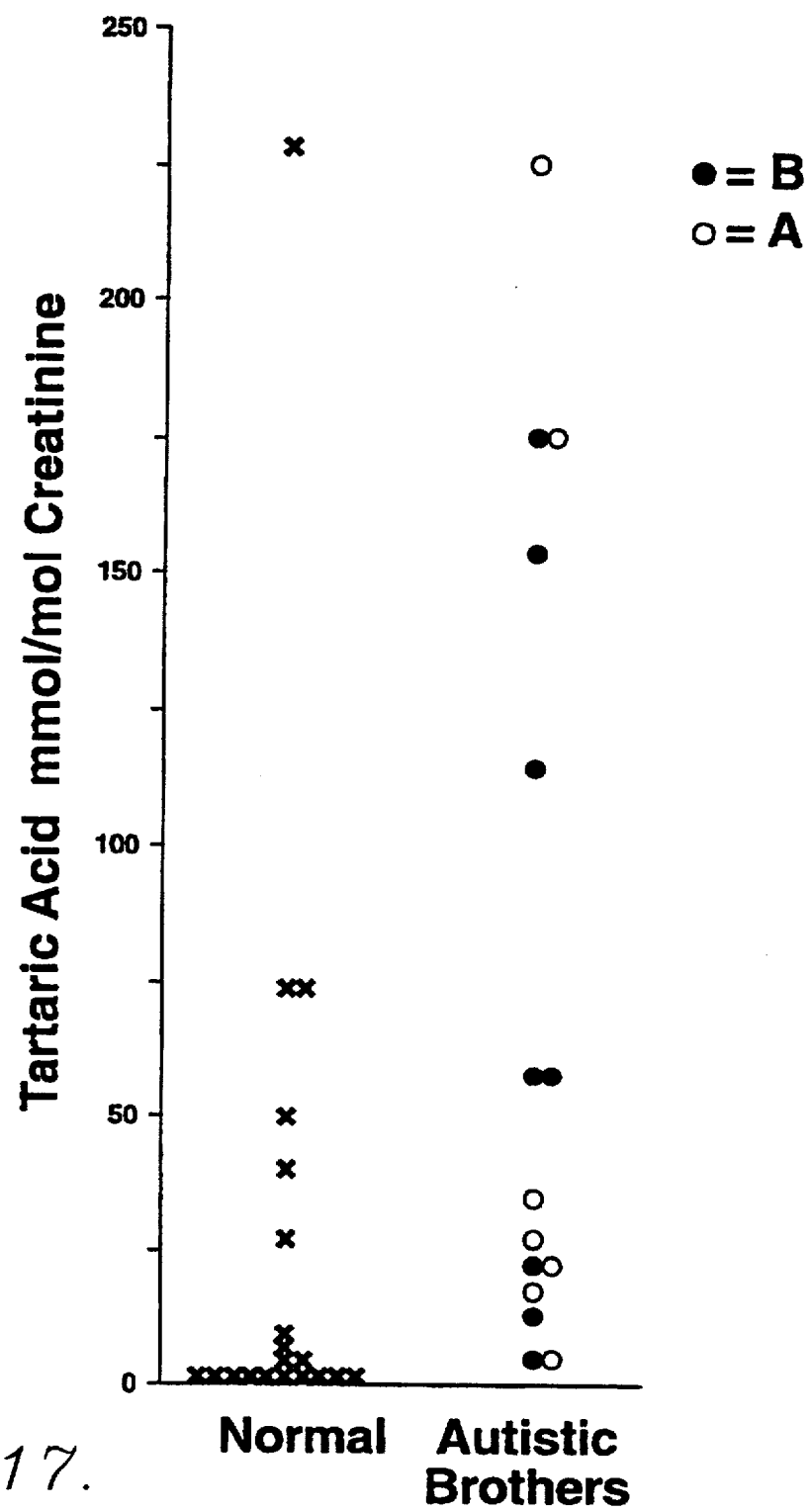
FIG. 17 is a comparative graph depicting the amounts of the TMS derivative of tartaric acid in normal patients and the autistic brothers referred to in Example 1.

Quantitation of tartaric acid. The distributions of tartaric acid concentrations are clearly different for the normal children and the brothers with autistic features (FIG. 17). Tartaric acid exceeds 20 mmol/mol creatinine in only 6 of 20 (30%) of the normal urines while tartaric acid is above this value in 15/17 (88%) of the urines from the brothers with autistic features. The mean value in the normal children is 26.6 mmol/mol creatinine (SD=26.6) while the mean value for the brothers with autistic features was 69.2 mmol/mol creatinine (SD=71.3). However, an inspection of the data clearly indicates a non-normal distribution of data for which median values provide a more meaningful comparison of the two groups. The median value of the normal urine group is 3 mmol/mol creatinine but is 36 mmol/mol creatinine in the brothers with autistic features.

Figure 18:
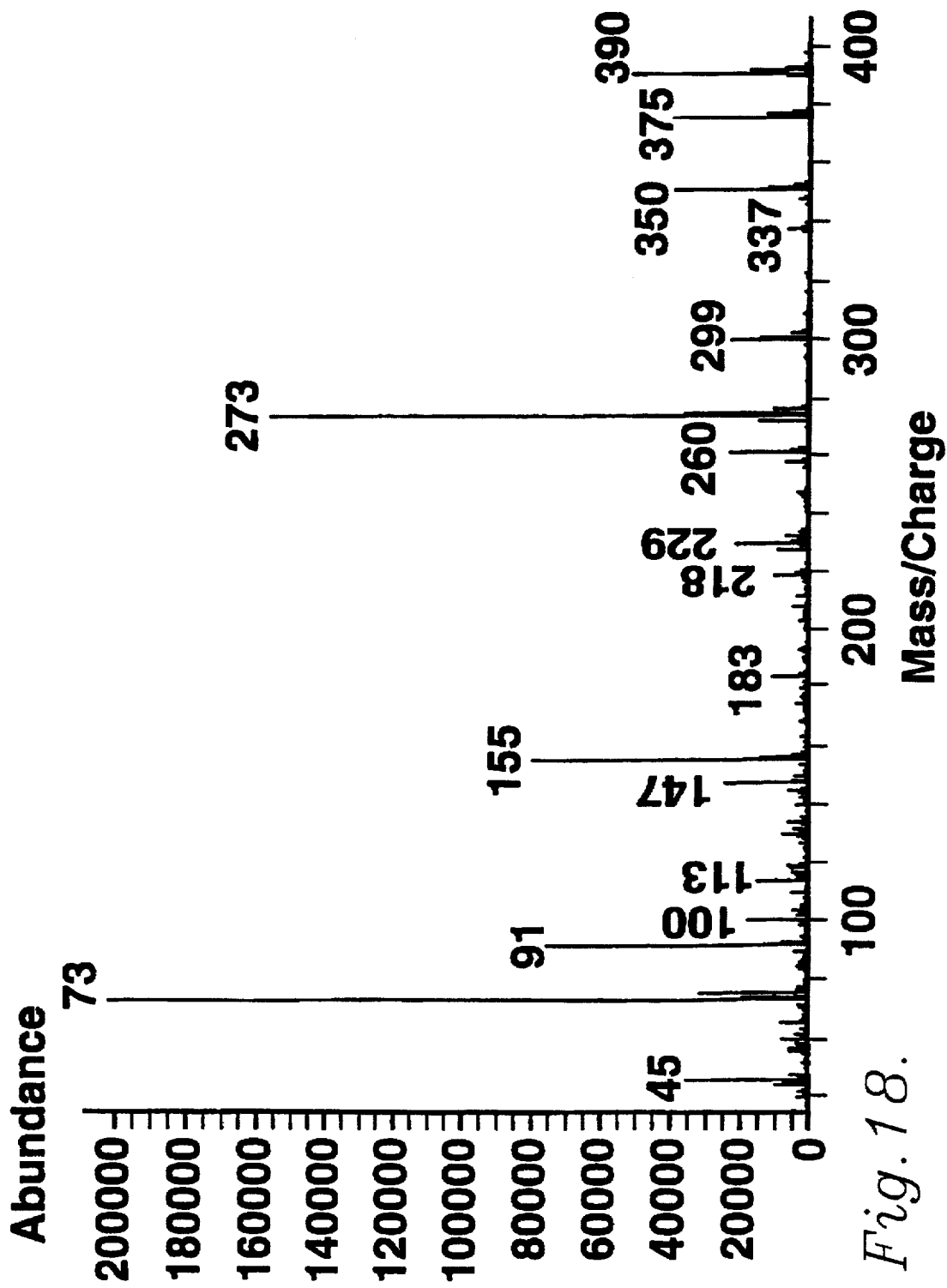
FIG. 18 is a GC/MS chromatogram giving the mass spectrum of the TMS derivative of a phenylcarboxylic acid found in high concentration in the urine samples of the brothers referred to in Example 1.
Figure 20:
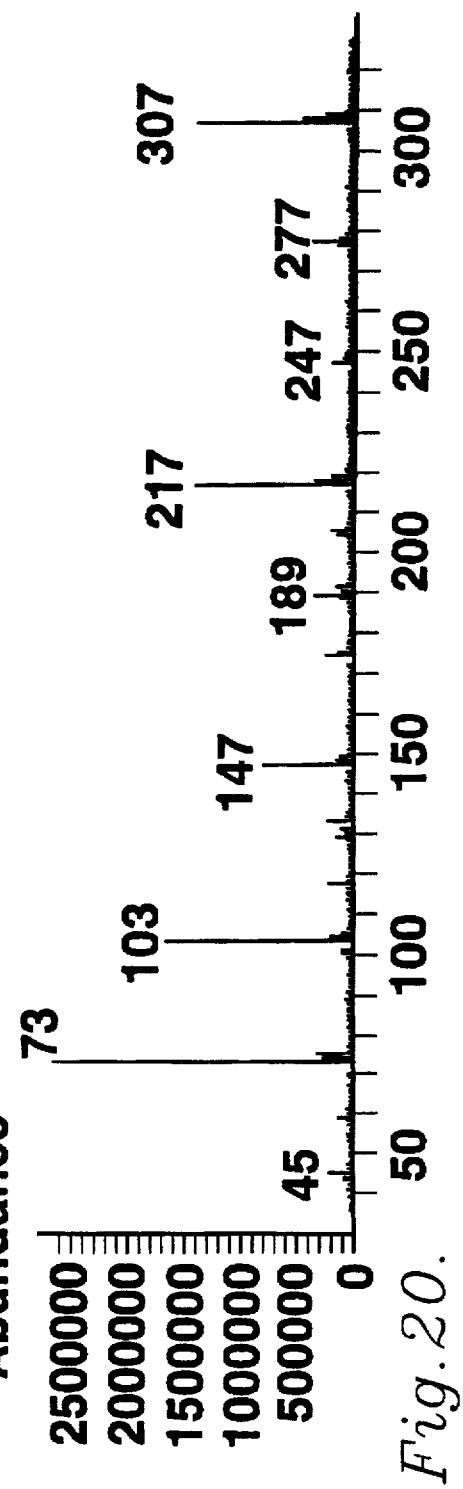
FIG. 20 is a GC/MS chromatogram giving the mass spectrum of the TMS derivative of arabinose found in the urine of the autistic brothers referred to in Example 1.
Figure 21:
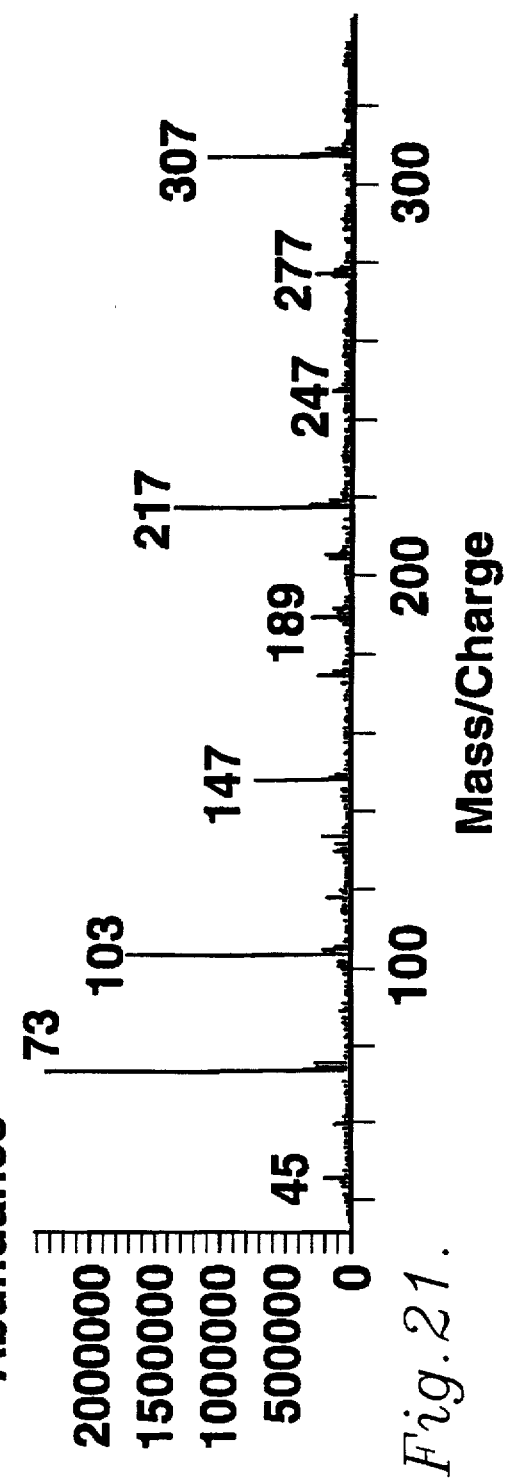
FIG. 21 is a GC/MS chromatogram giving the mass spectrum of the TMS derivative of authentic arabinose.

Identification of a phenylcarboxylic acid. The large peak at 18.86 min. has been found in extremely high concentrations in urine samples of the brothers with autistic features and in urine samples of some other children with autism and as a much smaller peak in most normal children. The spectrum of this compound is shown in FIG. 18. Ions at both m/z 73 and 147 indicate that this compound has at least two TMS groups. Other prominent ions are m/z 155, 273, 299, 350, 375, and 390. The use of perdeuterated TMS derivatives of this compound provides additional information about this compound (Table 2). The prominent ion at m/z 91 is consistent with the presence of the tropylium ion. An ion at m/z 65 is consistent with the loss of $CH_2CH_2$ from the tropylium ion. The ion at m/z 299 is due to the loss of a tropylium ion from the molecular ion at m/z 390. The ion at m/z 273 is consistent with a loss of COOTMS from the molecular ion, which clearly contains 2 TMS groups and, therefore, two functional groups. The additional functional group appears to be a hydroxyl group based on the ions at m/z 100 and 113. Thus, this compound is partially identified as a phenylcarboxylic acid.

tic compound (FIGS. 20–21). Both D- and L-arabinose have identical retention times and mass spectra.

Figure 22:
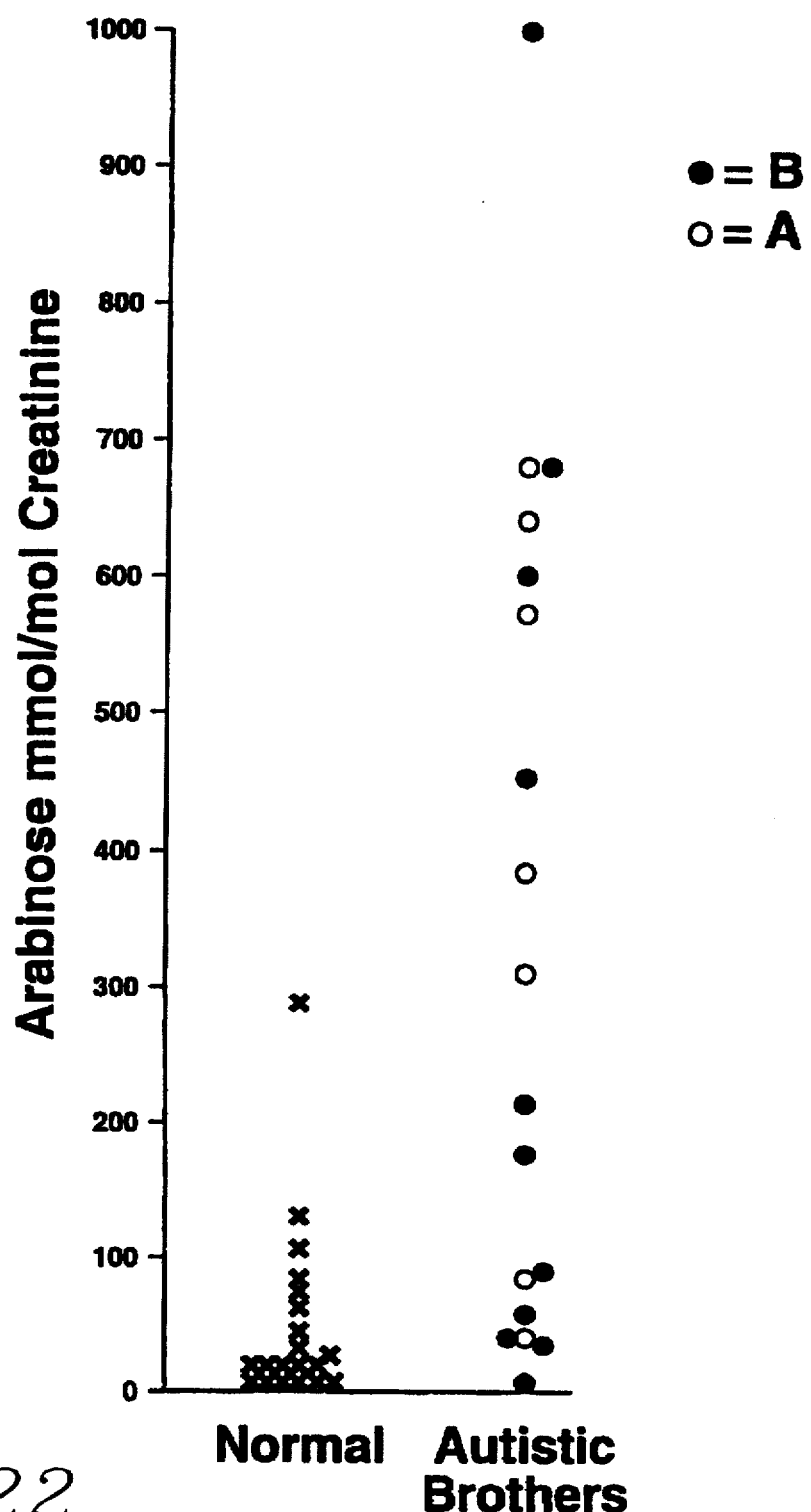
FIG. 22 is a comparative graph depicting the amounts of the TMS derivative of arabinose in normal patients and the autistic brothers referred to in Example 1.

Quantitation of arabinose. The mean concentration of arabinose in urine samples of normal children was 60.4 mmol/mol creatinine but an examination of the data in FIG. 22 shows that the data are not normally distributed since data points are much more frequent at the lower concentrations. The median value in the urine samples of normal children is 31.0 mmol/mol creatinine. The median value for the urine samples of the brothers with autistic features is 179 mmol/mol creatinine, nearly six times greater than the median value for the urine samples of the normal children. The mean value for the urine samples from the brothers with autistic features is 305 mmol/mol creatinine, five times the mean for the urine samples from normal children. The highest concentration of urine arabinose, 1008 mmol/mol creatinine was obtained in a sample from brother B.

Concentration of metabolites in maternal urine. The urine of the mother of the autistic brothers also had a somewhat unusual organic acid pattern in that the concentration of 3-oxoglutaric acid (6.1 mmol/mol creatinine) exceeded that of 2-oxoglutaric acid (5.3 mmol/mol creatinine). This same abnormal ratio was also found in several of the urine samples of the two brothers. The concentrations of arabinose (239 mmol/mol creatinine), the citric acid analog (74 mmol/mol creatinine), and the phenylcarboxylic acid compound (117 mmol/mol creatinine) were all elevated compared to normal children. The mother had no symptoms of autism.

Discussion

Figure 23:
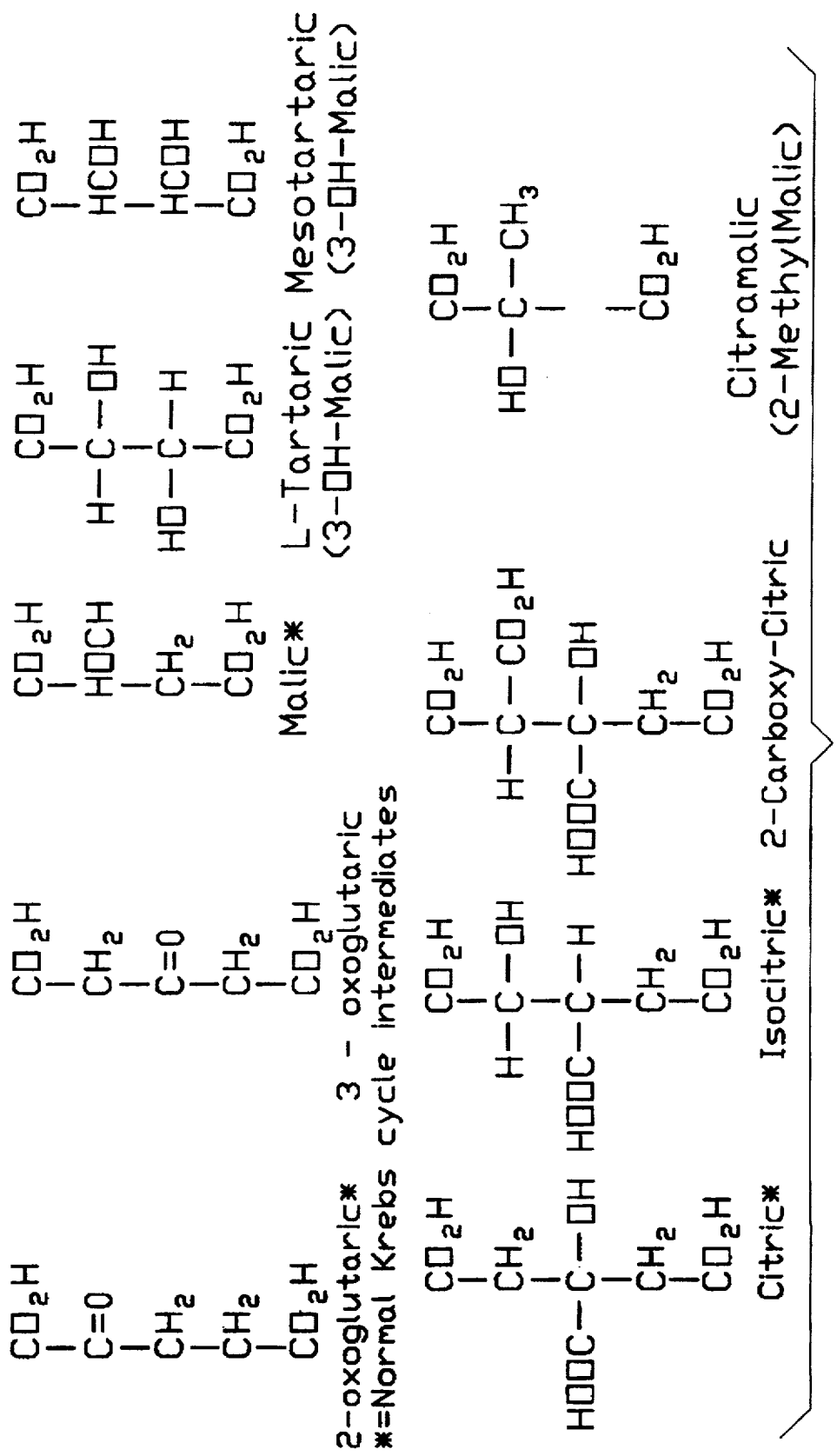
FIG. 23 sets forth the structures of normal and abnormal Krebs cycle compounds found in the urine samples of the autistic brothers referred to in Example 1.
Figure 24:
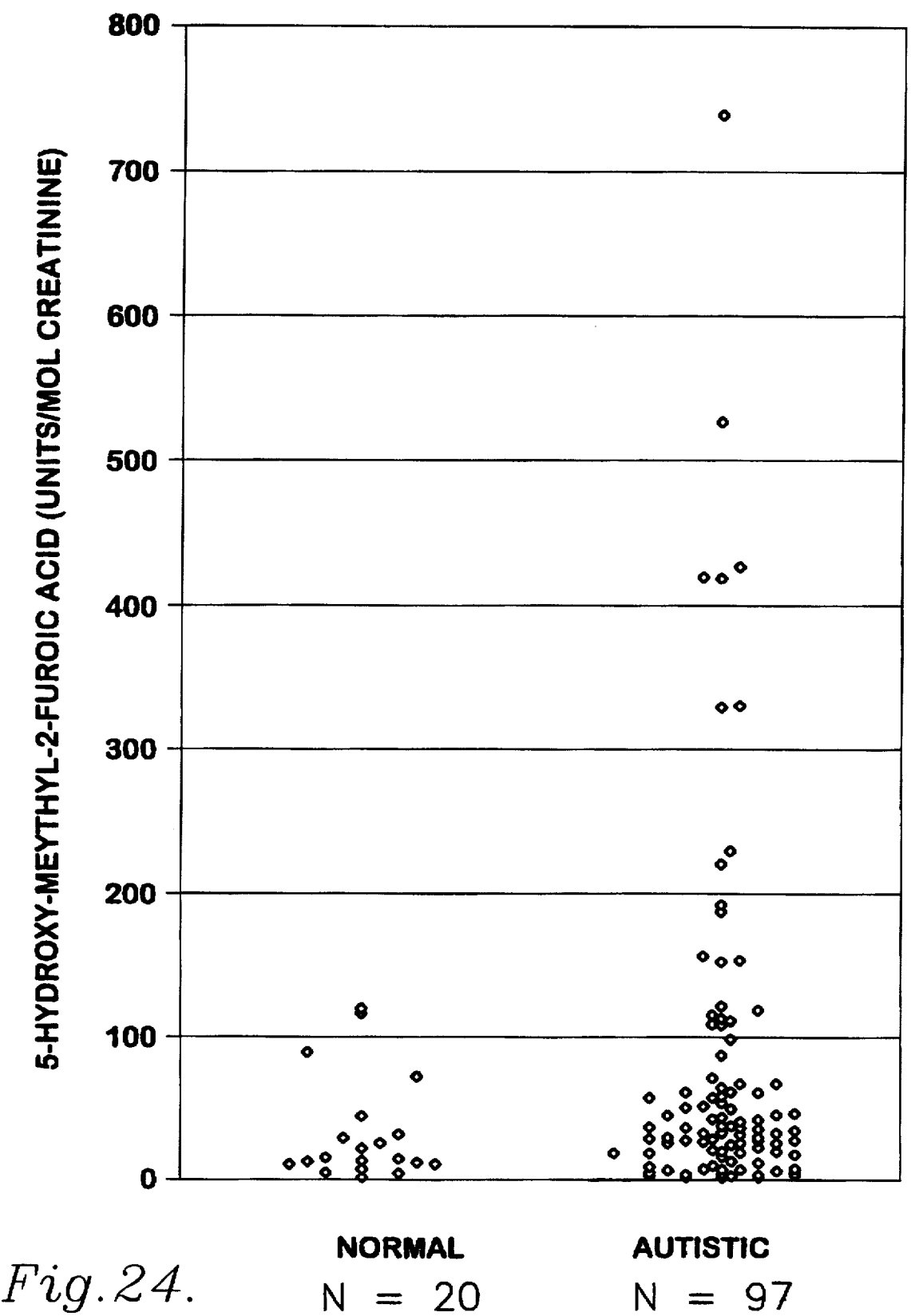
FIG. 24 is a comparative graph depicting the amounts of the TMS derivative of the 5-hydroxy-methyl-2-furoic acid in normal patients and in autistic patents referred to in Example 2.
Figure 25:
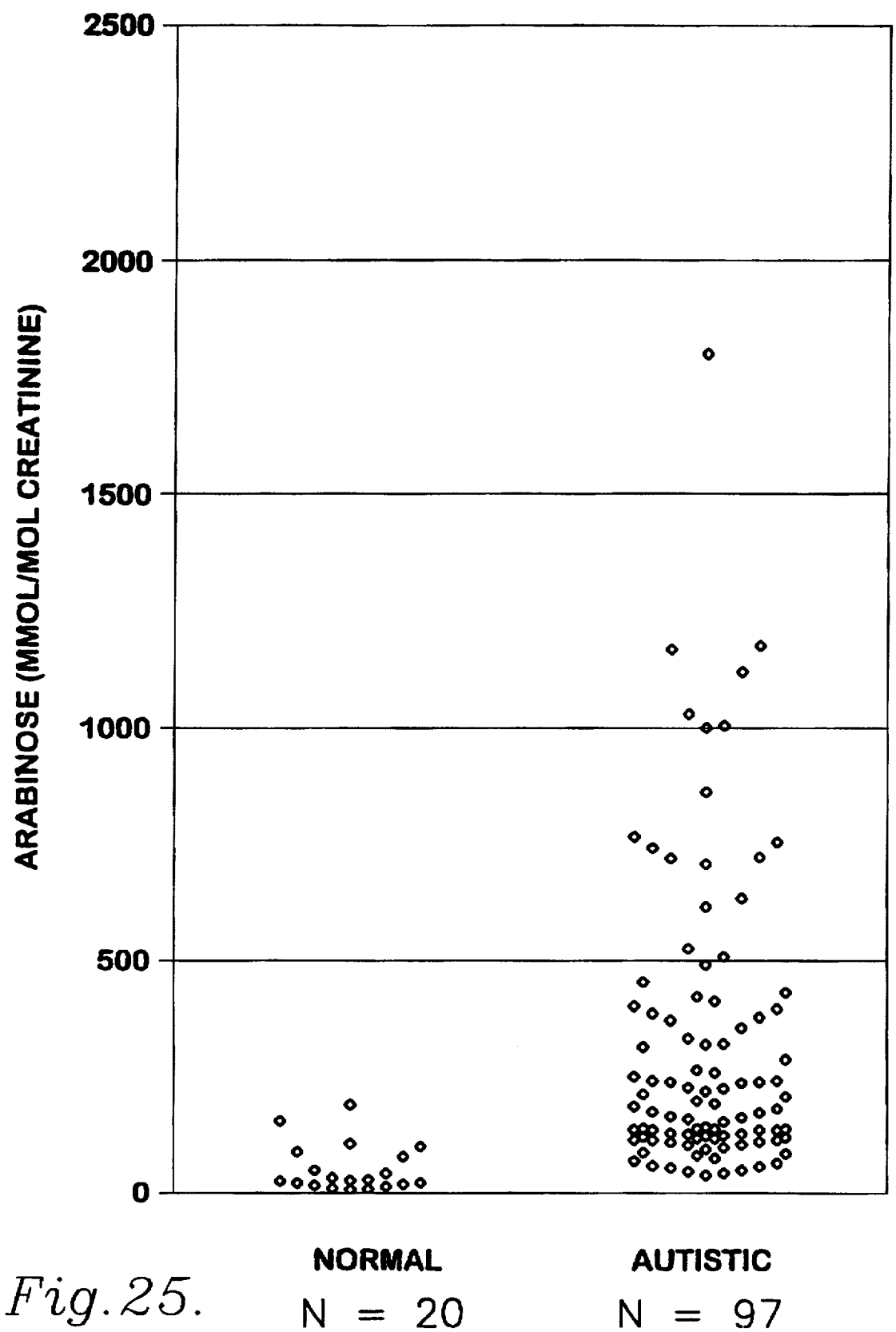
FIG. 25 is a comparative graph depicting the amounts of the TMS derivative of the arabinose in normal patients and in autistic patents referred to in Example 2.
Figure 26:
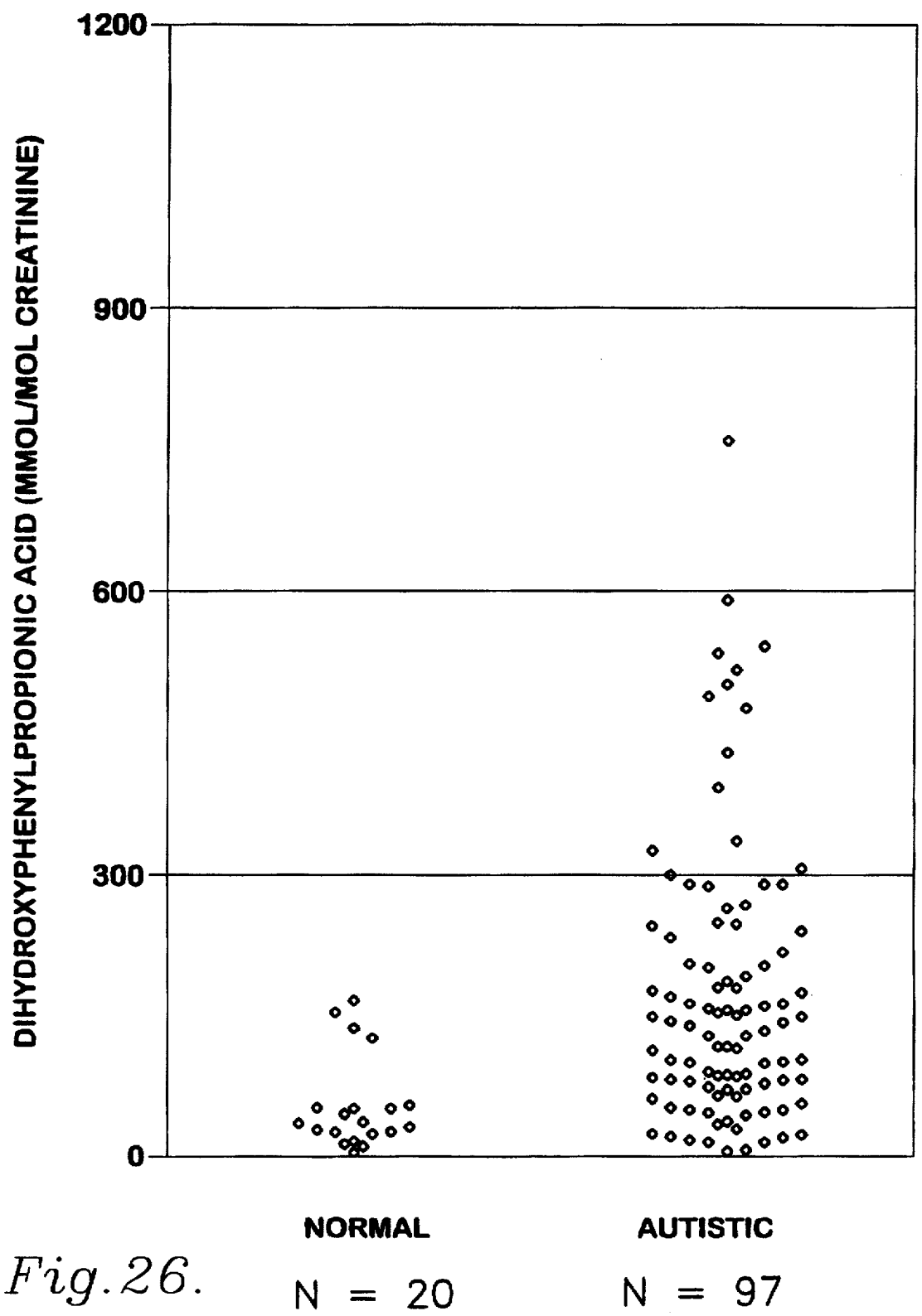
FIG. 26 is a comparative graph depicting the amounts of the TMS derivative of the dihydroxyphenylpropionic acid in normal patients and in autistic patents referred to in Example 2.
Figure 27:
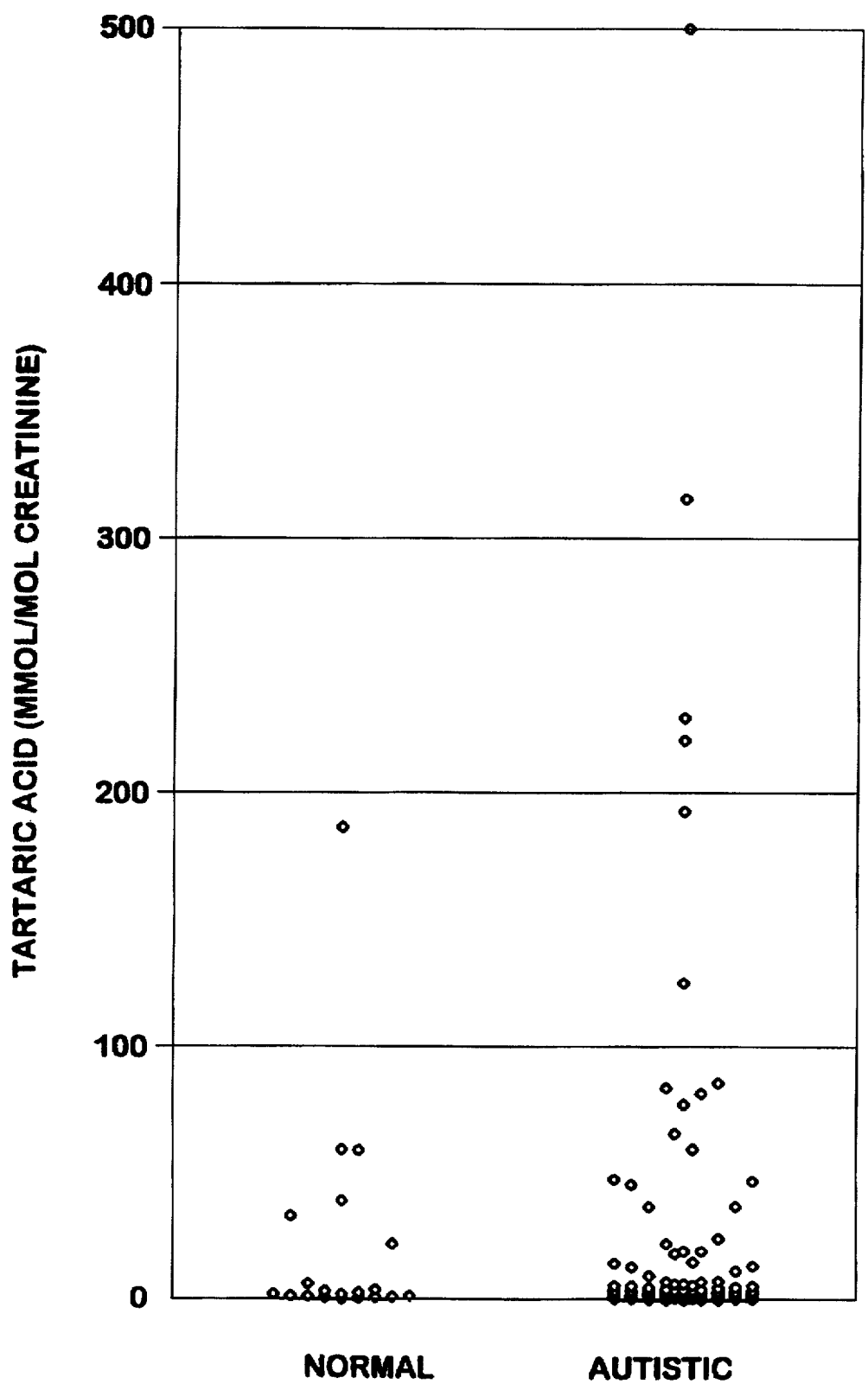
FIG. 27 is a comparative graph depicting the amounts of the TMS derivative of the tartaric acid in normal patients and in autistic patents referred to in Example 2.
Figure 28:
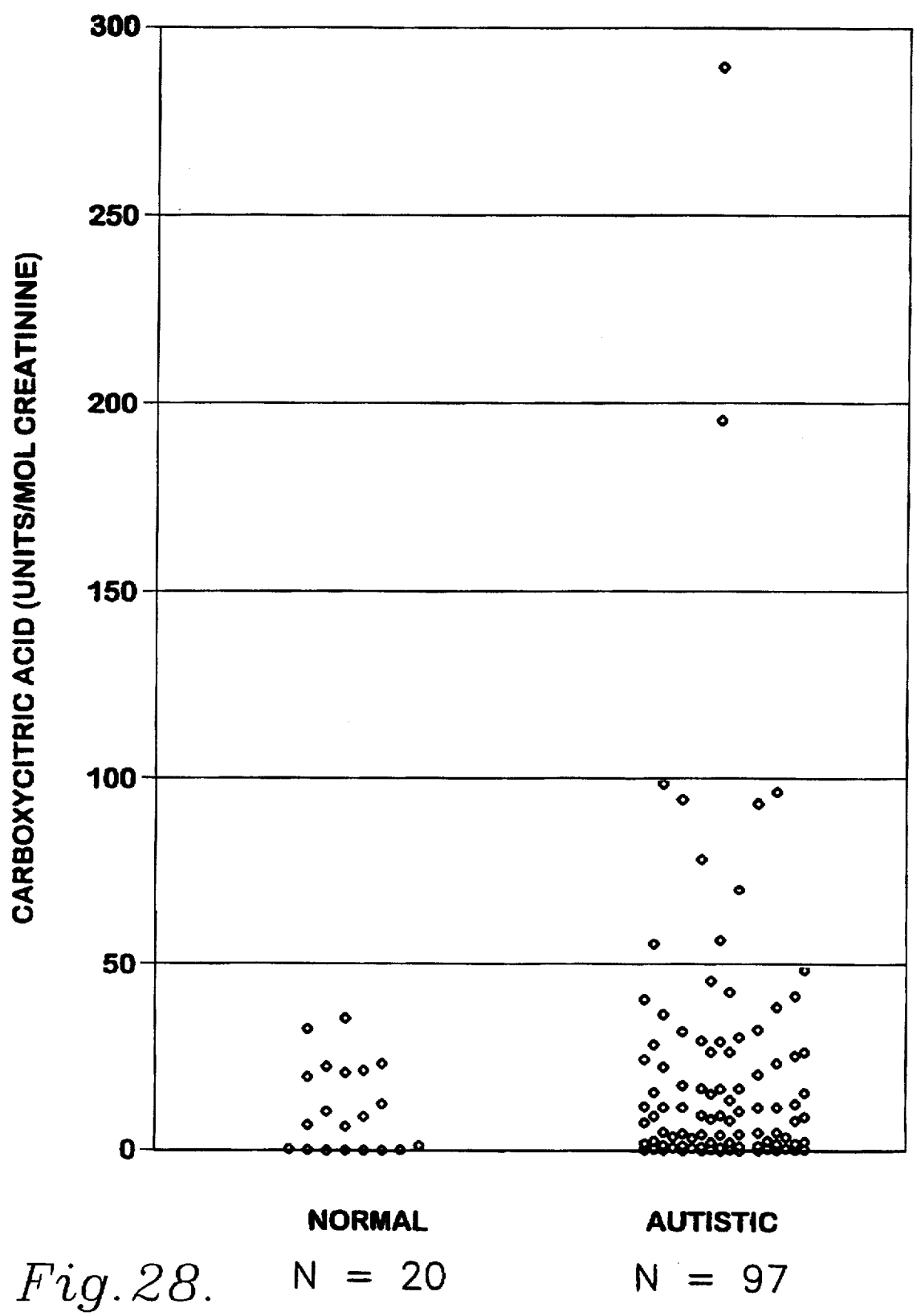
FIG. 28 is a comparative graph depicting the amounts of the TMS derivative of the carboxy citric acid in normal patients and in autistic patents referred to in Example 2.
Figure 29:
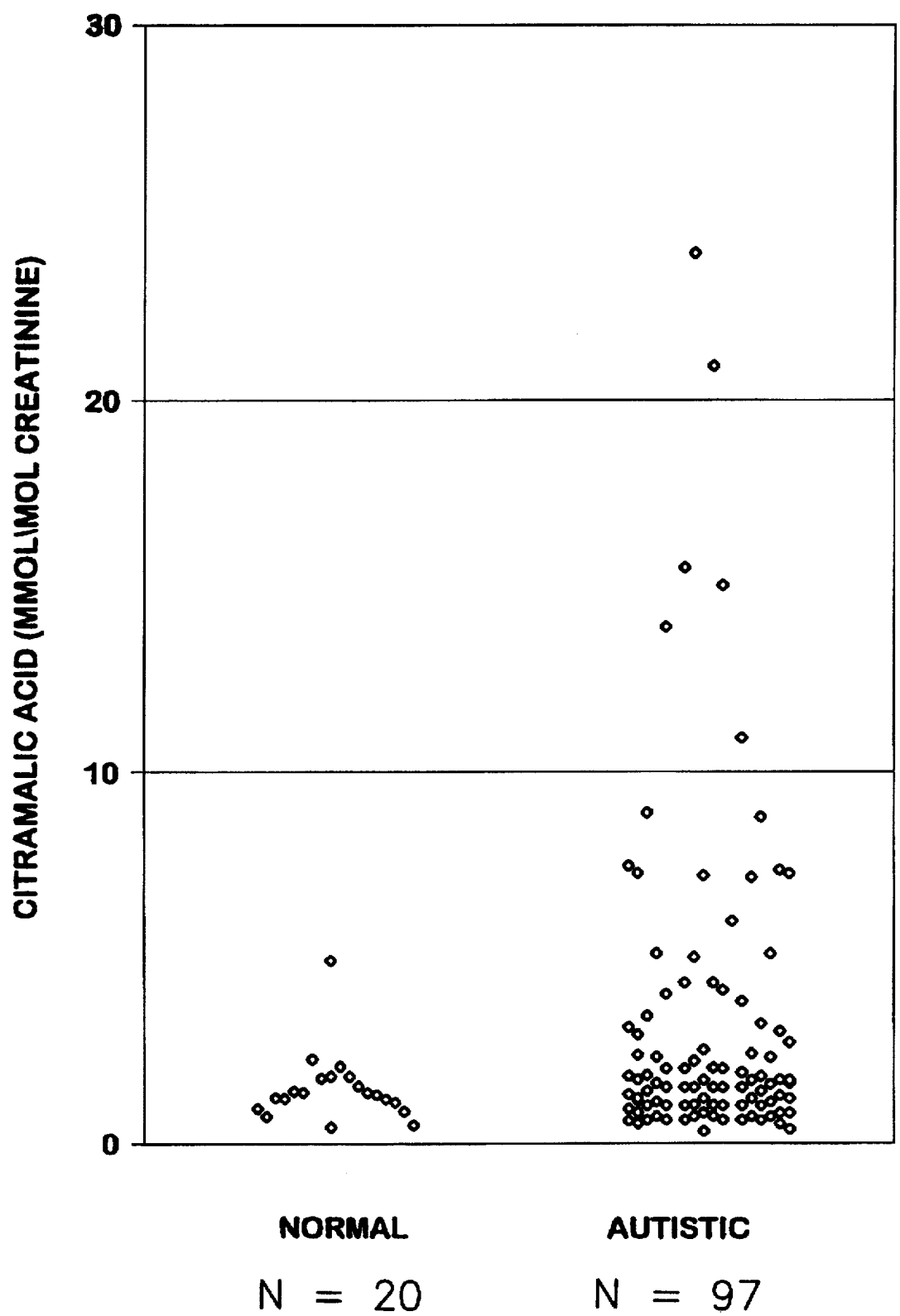
FIG. 29 is a comparative graph depicting the amounts of the TMS derivative of the citramalic acid in normal patients and in autistic patents referred to in Example 2.
Figure 30:
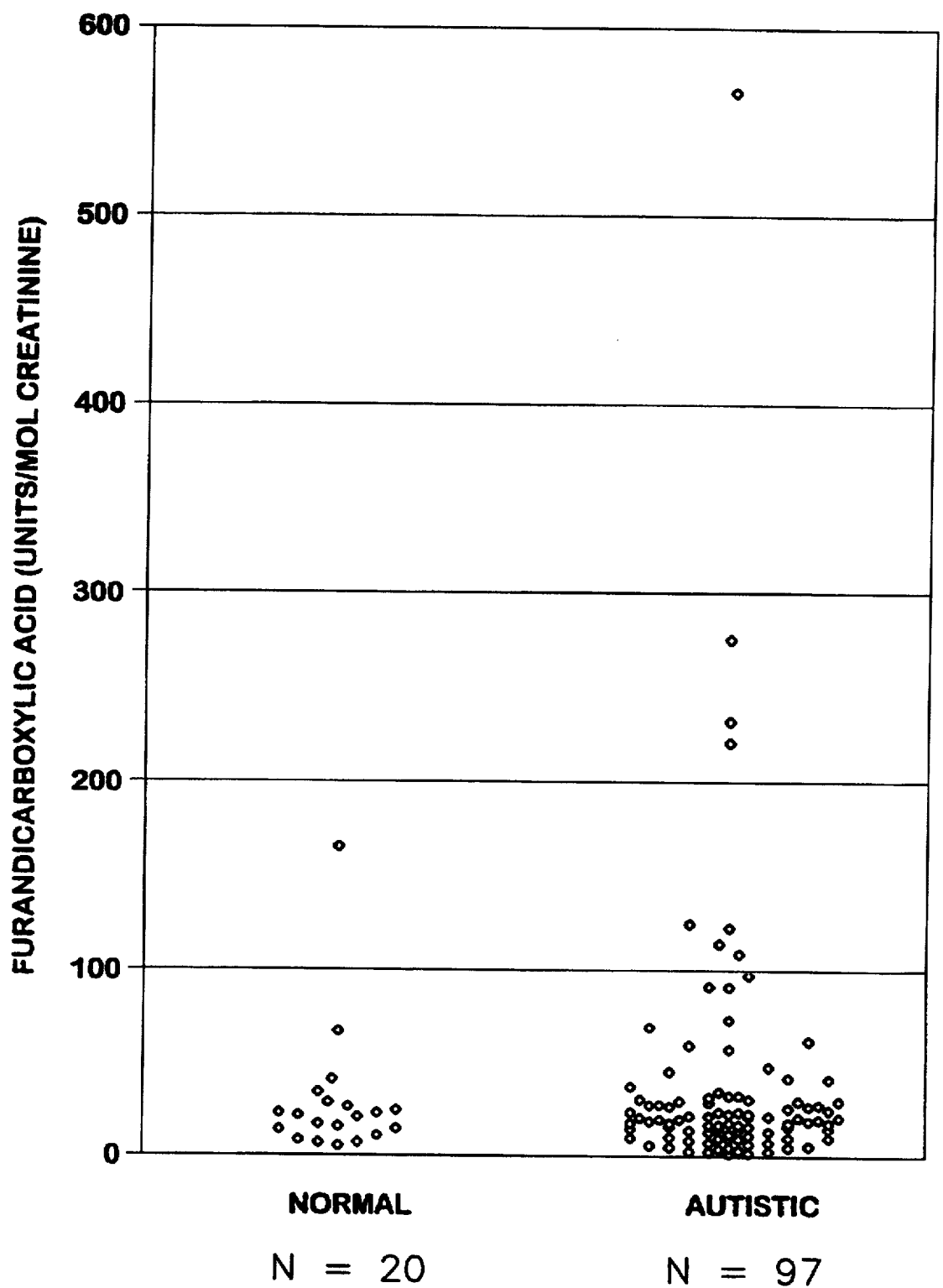
FIG. 30 is a comparative graph depicting the amounts of the TMS derivative of the furandicarboxylic acid in normal patients and in autistic patents referred to in Example 2.
Figure 31:
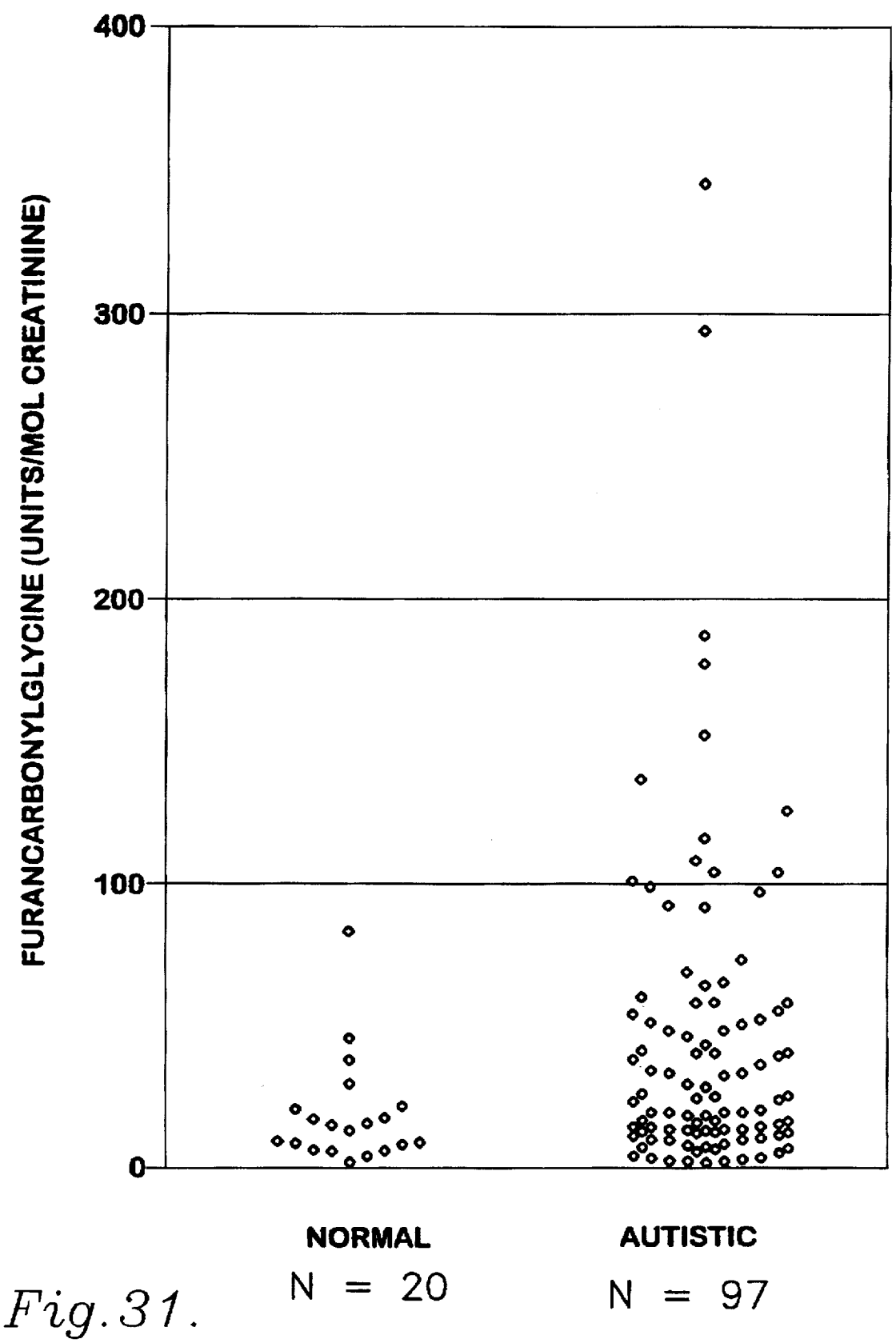
FIG. 31 is a comparative graph depicting the amounts of the TMS derivative of the furancarbonylglycine acid in normal patients and in autistic patents referred to in Example 2.

The structures of a number of compounds evaluated in this study are given in FIG. 23. The citric acid analog,

TABLE 2

| Mass loss from 390 | Major ions with plain TMS | Major ions d₂ TMS | Δ | TMS Content | Interpretation |
|---|---|---|---|---|---|
| 325 | 65 | 65 | 0 | 0 | $C_5H_5$ |
| 317 | 73 | 82 | 9 | 1 | TMS |
| 299 | 91 | 91 | 0 | 0 | $C_7H_7$ |
| 290 | 100 | 106 | 6 | 1 DMS | DMS—O—CH=CH |
| 277 | 113 | 122 | 9 | 1 TMS | TMS—O—$CH_2$—$CH_2$ |
| 243 | 147 | 162 | 15 | 1 TMS | TMS—O—DMS |
| 235 | 155 | 164 | 9 | 1 DMS | ? |
| 161 | 229 | 244 | 15 | 1 TMS 1 DMS | ? |
| 117 | 273 | 282 | 9 | 1 TMS | M—COOTMS |
| 91 | 299 | 317 | 18 | 2 TMS 1 DMS | M—$C_7$—$H_7$ |
| 53 | 337 | 355 | 18 | 2 TMS | M—$CH_2$CH=CHCH |
| 40 | 350 | 368 | 18 | 2 TMS 1 DMS | M—$CH_2$CH=CH |
| 15 | 375 | 390 | 15 | 1 TMS 1 DMS | M—$CH_3$ |
| 0 | 390 | 408 | 18 | 2 TMS | M |

Figure 19:
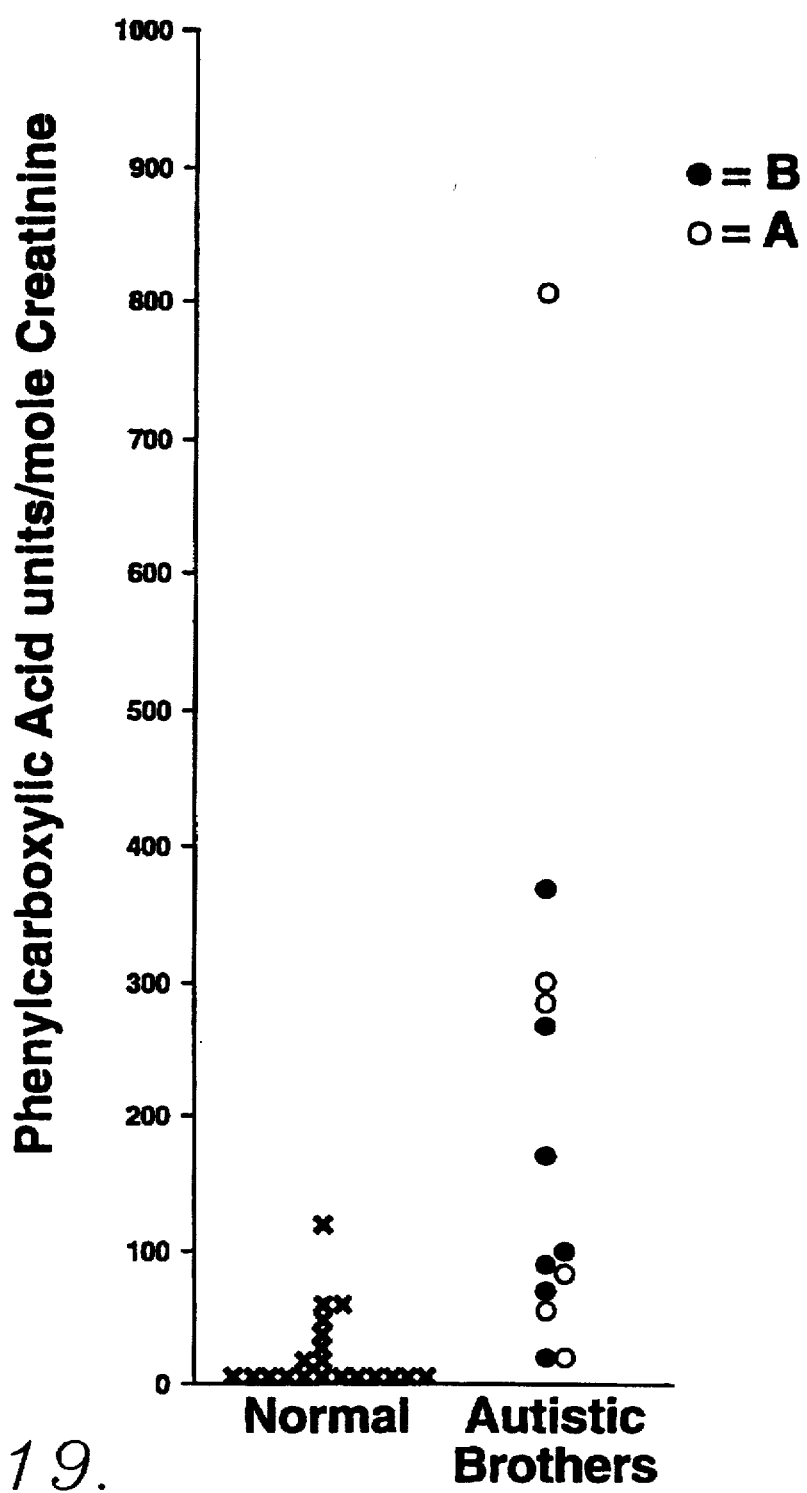
FIG. 19 is a comparative graph depicting the amounts of the TMS derivative of the phenylcarboxylic acid referred to in FIG. 16 in normal patients and the autistic brothers referred to in Example 1.

Quantitation of phenylcarboxylic acid compound. The concentration of the phenylcarboxylic acid was found in much higher values in the urine of the autistic brothers than in normal urine (FIG. 19). The concentration of this compound in 13 of 20 normal children is less than 10 units/mol creatinine while the concentration was as high as 800 units/mol creatinine in brother A. This compound was confirmed by identification of complete mass spectra in all of the normal children demonstrating that this compound is not a drug metabolite.

Identification of arabinose. The peak at 14.36 min. was identified as the TMS derivative of the carbo-hydrate arabinose based on comparison of its mass spectrum and retention time to those of the TMS derivative of the authentartaric, citramalic, and 3-oxo- glutaric acid are all analogs of Krebs cycle intermediates. (The structure of the citric acid analog is represented as 2-carboxycitric although the position of the extra carboxyl group has not been established.)

Elevated concentrations of citramalic acid appear to be clearly different than those in normal children since only one of the control children had a value greater than 2 mmol/mol creatinine. Citramalic acid, (2-methylmalic acid) and 3-methylmalic acid are analogs of the Krebs cycle intermediate malic acid and might interfere in the further metabolism of malic acid, leading to depletion of oxalacetic, the product of the action of malate dehydrogenase on malic acid. Oxalacetic acid is needed for condensation with acetic acid to replenish the Krebs cycle. A significant decrease in Krebs cycle activity could significantly impair cellular energy production. Very little information is available in the literature on citramalic acid or 3-methylmalic acid in biological fluids of humans. Citramalic acid was found in increased concentration in cerebrospinal fluid (CSF) samples of patients with bacterial meningitis but not in normal samples of CSF, CSF samples from febrile patients or from patients with aseptic meningitis (10). Citramalic acid has not been reported as a mammalian metabolite but has been reported to accumulate in respiration- deficient mutants of brewer's, baker's, and wine yeasts (11). Furthermore, an enzyme which catalyzes the condensation of acetyl coenzyme A (CoA) and pyruvate to form citramalic acid has been isolated from Baker's yeast (11). In addition, we have found citramalic to be consistently produced by *Propionobacteria acnes* cultures from human stool samples. A very large number of culture media from a wide variety of anaerobic bacteria isolated from stool samples by us were negative for citramalic acid production. It should also be noted that, although citramalic acid has not been reported as a mammalian metabolite, the possibility that it is of human origin cannot be ruled out.

The citric acid analog is a tentatively identified new molecule which was not previously known. The biosynthesis of several citric acid analogs has been reported as an ability of several species of fungi although the citric add analog is not one of the analogs reported to be produced by these spedes (12). A citric acid analog methylcitric acid, is produced in the disease propionic aoidemia when propionyl CoA instead of acetyl CoA condenses with oxalacetio acid (13). Carboxycitric add could hypothetically be formed by condensation of malonyl CoA instead of acetyl CoA with oxalacetic acid, resulting in the production of 2-carboxyoitdc acid.

Tartaric acid is another compound that appears to be abnormally elevated. However, unlike citramalic, some normal children excreted significant amounts of tartaric acid. Tartaric acid is an analog of malic acid and is a known inhibitor of the citric acid cycle enzyme fumarase (14), which catalyzes the interconversion of malate and fumarate. Tartaric acid is not known as a mammalian metabolite. It is most widely known as a byproduct of the wine industry in which special procedures are used to remove tartaric acid sediment. Tartaric acid is known as a metabolic product of Saccharomyces. Since this species is endogenous to grapes, it is not clear whether all tartaric acid is a yeast metabolic product or whether some is due to endogenous grape metabolism (15). Tartaric acid is present in all grape products such as grape juice, wine, grape jelly, and is used as a food additive (16). However, grape products were not commonly ingested by either of the siblings with autistic features. It is classified as GRAS (generally recognized as safe) by the United States Food and Drug Administration (16). Evidence of toxicity is conflicting. It has been reported to cause muscle weakness and renal impairment (17) which is of interest since the two brothers with autistic features had these symptoms at times.

Unfortunately, tartaric acid was not measured at the time these symptoms were present. The oral ingestion of as little as 12 grams of tartaric acid has been reported to cause a human fatality (18) while other studies indicate a much greater amount can be tolerated without causing toxicity (19–21). The guinea pig and pig are much more susceptible to renal damage by tartaric acid than the rat upon which much toxicological data have been gathered (22).

A compound with the same retention time and mass spectrum as arabinose was detected as present in high concentrations in the urine. Arabinose is present in a number of fruits but was not found as a major component of 72 individuals with pentosuria (23). The carbohydrate alcohol arabitol is a carbohydrate produced by Candida albicans (24). Measurement of arabitol in human blood and in animal blood has been used as an indicator of the extent of Candida infection(25). These other studies employed GC or GC/MS of TMS derivatives as in this study. However, the retention time on GC and the electron impact mass spectra of these compounds are so similar that it is not clear whether arabitol and arabinose were differentiated in these other studies but they were definitely differentiated in our study.

Example 2

In this example, urine samples from a larger number of autistic patients were analyzed for the presence of the abnormal metabolites referred to in Example 1. In addition, the urine samples from these patients were tested for other abnormal metabolites, namely 5-hydroxy-methyl-2-furoic acid, dihydroxyphenylpropionic acid (DHPPA), furandicarboxylic acid and furancarbonylglycine. In particular, urine samples from a total of 97 autistic patients were collected, as well as urine samples from a total of 20 normal individuals. These samples were collected at various times over an approximate one-year period.

Quantitation for these additional compounds (except for dihydroxyphenylpropionic acid) was performed by assigning the response of an average size ion chromatogram peak as 100 units and then calibrating all other peaks against these standards. Dihydroxyphenylpropionic acid was quantitated by using 3,4-dihydroxyphenylpropionic acid as the analytical standard. The rest of the test was performed exactly as described in Example 1.

FIGS. 24–31 illustrate the results of these tests. In each instance, at least certain of the urine samples from the autistic patients exhibited levels of the abnormal metabolites greatly in excess of the normals. This further indicates that the presence of these metabolites is an indicator of autism.

Example 3

In this example, an antifungal drug was administered to a total of 19 autistic children (each was classified as an autistic according to the latest criteria proposed by the American Psychiatric Association) in order to determine whether such therapy would have an effect on the levels of abnormal metabolites in the patients' urine. Certain of the marker compounds are related to those produced by fungi or yeast in culture, and it was hypothesized that the abnormally high presence of one or more of the marker compounds in the urine of autistic patients could be explained on the basis of infection or colonization of the patients with fungi or yeast.

In initial or baseline testing for the presence of abnormal metabolites, all of the patients exhibited above normal levels of at least certain of the metabolites. Each child was then treated with mycostatin (Nystatin) at a level of 100,000 units four times per day (a total of 400,000 units/day) for 10 days. At this point, urine samples were obtained from each patient and analyzed for abnormal metabolites. The results of this study are set forth below, where all quantitative data are in mmol of compound/tool creatinine in urine:

TABLE 3

| COMPOUNDS | Baseline | | | Nystatin | | | |
| --- | --- | --- | --- | --- | --- | --- | --- |
| | AVG. | MEDIAN | STDEV | AVG | MEDIAN | STDEV | TTEST |
| Citramalic | 3.95 | 1.70 | 5.52 | 2.52 | 1.40 | 3.57 | 0.15 |
| 5-OH-methyl-2-furoic | 139.13 | 58.00 | 181.37 | 56.59 | 16.50 | 129.74 | 0.05 |
| 3-oxo-glutaric | 16.50 | 0.00 | 69.31 | 0.22 | 0.00 | 0.94 | 0.16 |
| Furan-2,5-dicarboxylic | 55.77 | 26.00 | 75.94 | 16.87 | 10.00 | 19.64 | 0.01 |
| Tartaric | 27.51 | 4.20 | 72.80 | 15.31 | 1.80 | 45.81 | 0.06 |
| Furancarbonylglycine | 58.88 | 41.00 | 77.53 | 45.54 | 12.00 | 88.73 | 0.31 |
| Arabinose | 384.36 | 271.00 | 480.31 | 178.95 | 126.00 | 145.28 | 0.04 |
| DHPPA analog | 147.00 | 99.00 | 158.52 | 131.87 | 131.00 | 85.16 | 0.34 |
| Carboxycitric | 31.45 | 9.80 | 65.89 | 18.26 | 63.0 | 27.85 | 0.22 |
| Phenylcarboxylic | 24.33 | 8.70 | 30.69 | 46.06 | 14.00 | 57.04 | 0.05 |

This data establishes that administration of the antifungal drug materially decreases the amounts of abnormal metabolites (save for phenylcarboxylic acid) in the urine of the autistic patients. This is indirect evidence that the abnormal levels may be due to fungal infection of these patients.

The parents of the autistic patients also reported some amelioration of the symptoms of autism in the treated patients including decreased hyperactivity, better sleep patterns, less stereotypical behavior, better eye contact, increased socialization, more and better vocalization, and increased concentration and focus.

REFERENCES

1. Jaeken, J., Van Den Berghe, G.; An infantile autistic syndrome characterized by the presence of succinlypurines in body fluids. Lancet 1984; 2:1058–61.
2. Jaeken, J, Van Den Berghe, G.; Screening for inborn errors of purine synthesis [Letter]. Lancet 1989; 1:500.
3. Stone, R. L., Dimi, J., Barshop, B., Jaeken, J., Van Den Berghe, G., Zalkin, H., Dixon, J.; A mutation in adenylsuccinate lyase associated with mental retardation and autistic features. Nat Genet 1992; 1:59–63.
4. Balazs, A.; Current concept of autism. Orv Hetil 991; 132:2827–35.
5. Moreno, H., Borjas, L., Arvieta, A., Saez, L., Prassada, Estevez J., Bonilla, E.; Clinical heterogeneity of the autistic syndrome: a study of 60 families. Invest. Clin., 1992; 33:13–31.
6. Tanaka, K.., Heine, DG., West-Dull, A., Lowe, T.; Gas-chromatographic method of analysis of urinary organic acids. Clin. Chem., 1980; 26:1839–46.
7. Chalmers, R. A., Lawson, A. M.; Organic acids in man. New York: Chapman and Hall, 1982:123–5.
8. Larsen, K.; Creatinine assay by a reaction kinetic principle. Clin. Chim. Acta. 1972; 41:209–17.
9. Petersson, G.; Mass-spectrometry of hydroxydicarboxylic acids as trimethylsilyl derivatives. Rearrangement reactions. Organic Mass Spectrometry, 1972; 6:565–76.
10. Periman, S., Carr, S. A.; Citramalic acid in cerebrospinal fluid of patients with bacterial meningitis. Clin. Chem. 1984; 30:1209–12.
11. Amaha, M., Sai, T.; Some aspects of (−)- citramalic acid accumulation by respiration-deficient routants of yeast. Antonie van Leeuwenhoek, 1969; 35:G15–16 (Supplement Yeast Symposium)
12. Birkinshaw, J. H.; Special chemical products. In: Ainsworth GC, Sussman AS, eds. The fungi, an advanced treatise, vol. 1. New York: Academic Press, 1965:179–228.
13. Ando, T., Rasmussen, K., Wright, J., Nyhan, W.; Isolation and identification of methylcitrate, a major metabolic product of propionate in patients with propionic acidemia. J. Biol. Chem. 1972; 247:2200–4.
14. Mahler, H., Cordes, E.; Biological chemistry. New York: Harper and Row, 1966:525–53.
15. Budavari, S., O'Neil, M., Smith, A., Heckelman, P., eds. The merck index, 11th edition. Rahway, N.J.: Merck, 1989: 1433.
16. Lewis, R. J.; Food additives handbook. New York: Van Nostrand Reinhold, 1989: 417–8.
17. Webster, R.; Legal medicine and toxicology. Philadelphia: WB Saunders, 1930: 413–4.
18. Gosselin, R. E., Smith, R. P., Hodge, H. C.; Clinical toxicology of commercial products, 5th edition. Baltimore: Williams and Wilkins, 1984:200.
19. Chasseaud, L. F., Down, W. H., Kilpatrick, D.; Absorption and biotransformation of L (+)-tartaric acid in rats. Experentia 1977; 33:998–9.
20. Down, W. H., Sacharin, R. M., Chasseaud, W. F., Kirkpatrick, D., Franklin, E. R.; Renal and bone intake of tartaric acid in rats: comparison of L (+) and DL-forms. Toxicology 1977; 8:333–46.
21. Gold, H., Zahm, W.; A method for the evaluation of laxative agents in constipated human subjects with a study of the comparative laxative potency of fumarates, sodium tartrate, and magnesium acid citrate. J. Am. Pharm. Assoc., 1943; 32:173–8.
22. Ory, J., Larsen, J.; Metabolism of L (+)- and D (−)-tartaric acids in different animal species. Arch. Toxicol. Suppl., 1978; 1:351–3.
23. Hiatt, H., Pentosuria. In: Scriver C, Beaudet, A., Sly, W., Valle, D., eds. The metabolic basis of inherited disease, vol. 1, 6th edition. New York: McGraw Hill, 1989: 481–91.
24. Kiehn, T. E., Bernard, E. M., Gold, J. W., Armstrong, D. Candidiasis: detection by gas-liquid chromatography of D-arabinitol, a fungal metabolite in human serum. Science 1979; 206:577–80.
25. Cook, E.; Autism: review of neurochemical investigation. Synapse 1990; 6:292–308.

I claim:

1. A method of detecting autism-related compounds in a patient comprising the steps of:
obtaining from the patient a sample of a body fluid selected from the group consisting of urine, blood, saliva and cerebral spinal fluid;

analyzing said sample to determine the quantity therein of at least one compound selected from the group consisting of citramalic acid, 5-hydroxy-methyl-2-furoic acid, 3-oxo-glutaric acid, furan-2,5-dicarboxylic acid, tartaric acid, furancarbonylglycine, arabinose, dihydroxyphenylpropionic acid, carboxycitric acid and phenylcarboxylic acid; and correlating the quantity of said at least one compound with an autism condition or lack thereof in said patient.

2. The method of claim 1, including the step of determining if said quantity is abnormally high as compared with a normal quantity thereof found in the same type of body fluid from non-autistic individuals of approximately the same age.

3. The method of claim 1, said body fluid being urine.

4. The method of claim 3, including the step of determining if said quantity is abnormally high as compared with a normal quantity thereof found in urine from non-autistic individuals of the same age, the quantity of said compounds being abnormal if present in the urine sample in at least the following amounts, respectively:

(a) at least about 10 mmol citramalic acid/mol creatinine in said urine sample;

(b) at least about 100 mmol 5-hydroxy-methyl-2-furoic acid/mol creatinine in said urine sample;

(c) at least about 300 mmol arabinose/mol creatinine in said urine sample;

(d) at least about 100 mmol furan-2,5-dicarboxylic acid/mol creatinine in said urine sample (e) at least about 90 mmol tartaric acid/mol creatinine in said urine sample;

(f) at least about 100 mmol furancarbonylglycine/mol creatinine in said urine sample;

(g) at least about 1 mmol 3-oxo-glutaric acid/mol creatinine in said urine sample;

(h) at least about 250 mmol dihydroxyphenylpropionic acid/mol creatinine in said urine sample;

(i) at least about 50 mmol carboxycitdc acid/mol creatinine in said urine sample; and (j) at least about 100 mmol phenycarboxylic acid/mol creatinine in said urine sample.

5. The method of claim 1, including the step of analyzing said sample to determine the quantities of a plurality of said compounds therein.

6. The method of claim 1, including the step of collecting a plurality of said samples over a period of time.

7. The method of claim 6, said sample being a urine sample, and including the step of collecting individual urine samples on a daily basis over a period of at least seven days.

* * * * *